United States Patent [19]
Boone et al.

[11] Patent Number: 5,849,883
[45] Date of Patent: Dec. 15, 1998

[54] METHOD FOR PURIFYING GRANULOCYTE COLONY STIMULATING FACTOR

[75] Inventors: Thomas C. Boone, Newbury Park; Allan L. Miller, Glendale; Jeffrey W. Andresen, Ventura, all of Calif.

[73] Assignee: Amgen Inc., Thousand Oaks, Calif.

[21] Appl. No.: 647,391

[22] Filed: May 9, 1996

Related U.S. Application Data

[62] Division of Ser. No. 383,533, Feb. 1, 1995, abandoned, which is a continuation of Ser. No. 13,134, Feb. 3, 1993, abandoned, which is a continuation of Ser. No. 348,011, May 9, 1989, abandoned, which is a continuation-in-part of Ser. No. 193,857, May 13, 1988, abandoned.

[51] Int. Cl.$^6$ .............................. C07K 1/14; C07K 1/18; C07K 1/36; C07K 14/535
[52] U.S. Cl. ...................... 530/412; 530/416; 530/417; 530/351; 435/69.5
[58] Field of Search .................................. 530/351, 412, 530/416, 417; 435/69.5

[56] References Cited

U.S. PATENT DOCUMENTS

| | | | |
|---|---|---|---|
| 4,764,504 | 8/1988 | Johnson et al. | 514/12 |
| 4,810,643 | 3/1989 | Souza | 435/68 |
| 5,043,156 | 8/1991 | Matsumoto et al. | 530/351 |

FOREIGN PATENT DOCUMENTS

| | | | |
|---|---|---|---|
| 0010487 | 11/1989 | European Pat. Off. | 530/351 |
| 61-045010 | 8/1986 | Japan . | |

OTHER PUBLICATIONS

Marston. Biochem. J. 240:1–12, 1986.
Sofer et al. Biotechniques 1:198–203, 1983.
Colony Stimulating Factors, ed Dexter, 1990, pp. 82–90 and 92.
Metcalf, *Immunol. Cell. Biol* 65 (Pt. 1) 1987, pp. 35–43.
Van Brunt, *Bio/Technology*, vol. 7, 1989, p. 859.
Fujisawa et al, *Jpn, J Cancer Res.* 77, 1986, pp. 866–869.
Platzer et al, *Blut* 54, 1987, pp. 129–136.

*Primary Examiner*—Elizabeth C. Kemmerer
*Attorney, Agent, or Firm*—Craig A Crandall; Steven M Odre; Ron K Levy

[57] ABSTRACT

Processes for isolating and purifying granulocyte colony stimulating factor (G-CSF) from a G-CSF producing microorganism are disclosed. The simplified processes include steps of lysing the microorganism and separating insoluble material containing G-CSF from soluble proteinaceous material; extracting the material with deoxycholate (optionally); solubilizing and oxidizing the G-CSF in the presence of a denaturant solubilizing agent and an oxidizing agent; removing the denaturant solubilizing agent from the G-CSF; subjecting the G-CSF to ion exchange chromatography; and recovering the purified G-CSF; yet excludes other cumbersome purification steps.

7 Claims, 32 Drawing Sheets bovine G-CSF sequence
bgcsf.dna

```
  1 ACCCCCCTTG GCCCTGCCCG ATCCCTGCCC CAGAGCTTCC TGCTCAAGTG
 51 CTTAGAGCAA GTGAGGAAAA TCCAGGCTGA TGGGCCCGAG CTGCAGGAGA
101 GGCTGTGTGC CGCCCACAAG CTGTGCCACC CGGAGGAGCT GATGCTGCTC
151 AGCCACTCTC TGGGCATCCC CCAGGCTCCC CTAAGCAGCT GCTCCAGCCA
201 GTCCCTGCAG CTGCCAGGCT GCCTGAACCA ACTACACGGC GGCCTCTTTC
251 TCTACCAGGG CCTCCTGCAG GCCCTGGGCG GCATCTCCCC AGAGCTGGCC
301 CCCACCTTGG ACACACTGCA GCTGGACGTC ACTGACTTTG CCACGAACAT
351 CTGGCTGCAG ATGGAGGACC TGGGGGCGGC CCCCGCTGTG CAGCCCACCC
401 AGGGCCCCAT GCCGACCTTC ACTTCAGCCT TCCAACGCAG AGCAGGAGGG
451 GTCCTGGTTG CTTCCCAGCT GCATCGTTTC CTGGAGCTGG CATACCCTGG
501 CCTGCGCTAC CTTGCTGAGC CCTGA
```

FIG.2A

```
  1  Thr Pro Leu Gly Pro Ala Arg Ser Leu Pro Gln Ser Phe Leu Leu
 46  Lys Cys Leu Glu Gln Val Arg Lys Ile Gln Ala Asp Gly Ala Glu
 91  Leu Gln Glu Arg Leu Cys Ala Ala His Lys Leu Cys His Pro Glu
136  Glu Leu Met Leu Leu Arg His Ser Leu Gly Ile Pro Gln Ala Pro
181  Leu Ser Ser Cys Ser Ser Gln Ser Leu Gln Leu Arg Gly Cys Leu
226  Asn Gln Leu His Gly Gly Leu Phe Leu Tyr Gln Gly Leu Leu Gln
271  Ala Leu Ala Gly Ile Ser Pro Glu Leu Ala Pro Thr Leu Asp Thr
316  Leu Gln Leu Asp Val Thr Asp Phe Ala Thr Asn Ile Trp Leu Gln
361  Met Glu Asp Leu Gly Ala Ala Pro Ala Val Gln Pro Thr Gln Gly
406  Ala Met Pro Thr Phe Thr Ser Ala Phe Gln Arg Arg Ala Gly Gly
451  Val Leu Val Ala Ser Gln Leu His Arg Phe Leu Glu Leu Ala Tyr
496  Arg Gly Leu Arg Tyr Leu Ala Glu Pro End
```

FIG. 3B bGCSF dna

```
                                                              30                                                  60
TTC TAG AAA AAA CCA AGG AGG TAA TAA ATA ATG ACT CCG CTG GGT CCG GCA CGT TCT CTG
Phe End Lys Lys Pro Arg Arg End End Ile Met Thr Pro Leu Gly Pro Ala Arg Ser Leu 90                                                 120
CCG CAG TCT TTC CTG CTG AAA TGC CTG GAA CAG GTT CGT AAA ATC CAG GCT GAC GGT GCA
Pro Gln Ser Phe Leu Leu Lys Cys Leu Glu Gln Val Arg Lys Ile Gln Ala Asp Gly Ala 150                                                 180
GAG CTC CAG GAA CGT CTG TGC GCT GCG CAC AAA CTG TGC CAC CCG GAA GAG CTG ATG CTG
Glu Leu Gln Glu Arg Leu Cys Ala Ala His Lys Leu Cys His Pro Glu Glu Leu Met Leu 210                                                 240
CTC CGT CAC TCT CTG GGT ATC CCG CAG GCG CCG CAG CTG TCT TCC TGC TCT TCC CAG TCT CTG
Leu Arg His Ser Leu Gly Ile Pro Gln Ala Pro Gln Leu Ser Ser Cys Ser Ser Gln Ser Leu 270                                                 300
CAG CTC CGT GGT TGC CTG AAC CAG CTC CAT GGT GGC CTG TTC CTG TAC CAG GGT CTG CTC
Gln Leu Arg Gly Cys Leu Asn Gln Leu His Gly Gly Leu Phe Leu Tyr Gln Gly Leu Leu 330                                                 360
CAA GCT TTG GCA GGT ATC TCT CCG GAA CTG GCT CCG ACC CTG GAC ACC CTG CAG CTC GAC
Gln Ala Leu Ala Gly Ile Ser Pro Glu Leu Ala Pro Thr Leu Asp Thr Leu Gln Leu Asp 390                                                 420
GTT ACC GAC TTC GCT ACC AAC ATC TGG CTG CAG ATG GAA GAT CTG GGT GCT GCA CCG GCG
Val Thr Asp Phe Ala Thr Asn Ile Trp Leu Gln Met Glu Asp Leu Gly Ala Ala Pro Ala 450                                                 480
GTT CAG CCG ACC CAG GGC GCT ATG CCG GCC TTC ACC TCT GCT TTC CAG CGT CGC GCT GGT
Val Gln Pro Thr Gln Gly Ala Met Pro Ala Phe Thr Ser Ala Phe Gln Arg Arg Ala Gly 510                                                 540
GGC GTT CTG GTA GCT TCT CAG CTG CAC CGT TTC CTC GAG CTG GCT TAC CGT GGT CTG CGT
Gly Val Leu Val Ala Ser Gln Leu His Arg Phe Leu Glu Leu Ala Tyr Arg Gly Leu Arg

TAC CTG GCT GAA CCG TAA TAG GAT CC
Tyr Leu Ala Glu Pro End End Asp
```

FIG.4 bGCSF dna4

```
         10         20         30        |40         50         60
    CTAGAAAA  AACCAAGGAG  GTAATAAATA  ATGACTCGC  TCGGCCCTGC  ACGTTCTCTG
    TTTT      TTGGTTCCTC  CATTATTTAT  TACTGAGGCG  AGCCGGGACG  TGCAAGAGAC

70        |80         90        100        110        |120
    CCGCAGAGCT  TCCTGCTGAA  ATGCCTCGAA  CAGGTTCGTA  AAATTCAGGC  TGATGGTGCT
    GGCGTCTCGA  AGGACGACTT  TACGGAGCTT  GTCCAAGCAT  TTTAAGTCCG  ACTACCACGA 130        140        150        |160        170        180
    GAGCTCCAGG  AGCGTCTGTG  CGCTGCTCAC  AAGCTCTGCC  ACCCTGAAGA  ACTCATGCTG
    CTCGAGGTCC  TCGCAGACAC  GCGACGAGTG  TTCGAGACGG  TGGGACTTCT  TGAGTACGAC

190|       200        210        220        230|       240
    CTCCGTCACT  CTCTGGGGAT  CCCGCAGGCG  CCGCTGTCTT  CTTGCTCCTC  TCAGTCTCTG
    GAGGCAGTGA  GAGACCCCTA  GGGCGTCCGC  GGCGACAGAA  GAACGAGGAG  AGTCAGAGAC 250        260        270        280        290        300
    CAACTCCGTG  GTTGCCTGAA  CCAGCTCCAT  GGTGGCCTGT  TCCTGTACCA  GGGTCTCCTG
    GTTGAGGCAC  CAACGGACTT  GGTCGAGGTA  CCACCGGACA  AGGACATGGT  CCCAGAGGAC 310        320        330       |340        350        360
    CAAGCTTTGG  CAGGCATCTC  TCCGGAACTC  GCACCTACTC  TCGATACTCT  GCAGCTCGAC
    GTTCGAAACC  GTCCGTAGAG  AGGCCTTGAG  CGTGGATGAG  AGCTATGAGA  CGTCGAGCTG 370        380        390        400        410        420
    GTTACCGACT  TCGCTACCAA  CATTTGGCTC  CAGATGGAAG  ATCTGGGCGC  TGCACCGGCT
    CAATGGCTGA  AGCGATGGTT  GTAAACCGAG  GTCTACCTTC  TAGACCCGCG  ACGTGGCCGA

430       |440        450        460       |470        480
    GTTCAGCCGA  CTCAGGGCGC  TATGCCTACC  TTCACCTCTG  CTTTCCAGCG  TCGTGCTGGT
    CAAGTCGGCT  GAGTCCCGCG  ATACGGATGG  AAGTGGAGAC  GAAAGGTCGC  AGCACGACCA

490       ,500        510        520        |530        540
    GGTGTTCTGG  TAGCTTCTCA  GCTGCACCGT  TTCCTCGAGC  TGGCTTACCG  TGGTCTGCGT
    CCACAAGACC  ATCGAAGAGT  CGACGTGGCA  AAGGAGCTCG  ACCGAATGGC  ACCAGACGCA 550        560
    TACCTGGCTG  AACCGTAATA  G
    ATGGACCGAC  TTGGCATTAT  CTTAA
```

FIG. 5 bGCSF dna4            bGCSF    SUBUNIT I    Xba1-HindIII

```
          12          22          32          42          52          62
CTAGAAAAAA CCAAGGAGGT AATAAATAAT GACTCCGCTC GGCCCTGCAC GTTCTCTGCC
TTTTTT     GGTTCCTCCA TTATTTATTA CTGAGGCGAG CCGGGACGTG CAAGAGACGG 72          82          92         102         112         122
GCAGAGCTTC CTGCTGAAAT GCCTCGAACA GGTTCGTAAA ATTCAGGCTG ATGGTGCTGA
CGTCTCGAAG GACGACTTTA CGGAGCTTGT CCAAGCATTT TAAGTCCGAC TACCACGACT 132         142         152         162         172         182
GCTCCAGGAG CGTCTGTGCG CTGCTCACAA GCTCTGCCAC CCTGAAGAAC TCATGCTGCT
CGAGGTCCTC GCAGACACGC GACGAGTGTT CGAGACGGTG GGACTTCTTG AGTACGACGA 192         202         212         222         232         242
CCGTCACTCT CTGGGGATCC CGCAGGCGCC GCTGTCTTCT TGCTCCTCTC AGTCTCTGCA
GGCAGTGAGA GACCCCTAGG GCGTCCGCGG CGACAGAAGA ACGAGGAGAG TCAGAGACGT 252         262         272         282         292         302
ACTCCGTGGT TGCCTGAACC AGCTCCATGG TGGCCTGTTC CTGTACCAGG GTCTCCTGCA
TGAGGCACCA ACGGACTTGG TCGAGGTACC ACCGGACAAG GACATGGTCC CAGAGGACGT
```

TCGA

FIG. 6A bGCSF dna4    bGCSF SUBUNIT II    HindIII-EcoR1

```
      312         322         332         342         352         362
AGCTTTGGCA GGCATCTCTC CGGAACTCGC ACCTACTCTC GATACTCTGC AGCTCGACGT
           CCGTAGAGAG GCCTTGAGCG TGGATGAGAG CTATGAGACG TCGAGCTGCA 372         382         392         402         412         422
TACCGACTTC GCTACCAACA TTTGGCTCCA GATGGAAGAT CTGGGCGCTG CACCGGCTGT
ATGGCTGAAG CGATGGTTGT AAACCGAGGT CTACCTTCTA GACCCGCGAC GTGGCCGACA 432         442         452         462         472         482
TCAGCCGACT CAGGGCGCTA TGCCTACCTT CACCTCTGCT TTCCAGCGTC GTGCTGGTGG
AGTCGGCTGA GTCCCGCGAT ACGGATGGAA GTGGAGACGA AAGGTCGCAG CACGACCACC 492         502         512         522         532         542
TGTTCTGGTA GCTTCTCAGC TGCACCGTTT CCTCGAGCTG GCTTACCGTG GTCTGCGTTA
ACAAGACCAT CGAAGAGTCG ACGTGGCAAA GGAGCTCGAC CGAATGGCAC CAGACGCAAT 552         562
CCTGGGCTGA CCGTAATAG
GGACCGACTT GGCATTATCT TAA
```

FIG. 6B

```
bGCSF dna4
                                 30                                    60
  C TAG AAA AAA CCA AGG AGG TAA TAA ATA ATG ACT CCG CTC GGC CCT GCA CGT TCT CTG
                                         Met Thr Pro Leu Gly Pro Ala Arg Ser Leu 90                                   120
CCG CAG AGC TTC CTG CTG AAA TGC CTC GAA CAG GTT CGT AAA ATT CAG GCT GAT GGT GCT
Pro Gln Ser Phe Leu Leu Lys Cys Leu Glu Gln Val Arg Lys Ile Gln Ala Asp Gly Ala 150                                   180
GAG CTC CAG GAG CGT CTG TGT GCT CAC AAG CTC TGC CAC CCT GAA GAA CTC ATG CTG
Glu Leu Gln Glu Arg Leu Cys Ala Ala His Lys Leu Cys His Pro Glu Glu Leu Met Leu 210                                   240
CTC CGT CAC TCT CTG GGG ATC CCG CAG GCG CCG CTG TCT TGC CAC CCT CAG TCT CTG
Leu Arg His Ser Leu Gly Ile Pro Gln Ala Pro Leu Ser Cys His Pro Gln Ser Leu 270                                   300
CAA CTC CGT GGT TGC CTG AAC CAG CTC CAT GGT GGC CTG TTC CTG TAC CAG GGT CTC CTG
Gln Leu Arg Gly Cys Leu Asn Gln Leu His Gly Gly Leu Phe Leu Tyr Gln Gly Leu Leu 330                                   360
CAA GCT TTG GCA GGC ATC TCT CCG GAA CTC GCA CCT ACT CTC GAT GAA CTC CAG CTC GAC
Gln Ala Leu Ala Gly Ile Ser Pro Glu Leu Ala Pro Thr Leu Asp Glu Leu Gln Leu Asp 390                                   420
GTT ACC GAC TTC GCT ACC AAC ATT TGG CTC CAG ATG GAA GAT CTG GGC GCT GCA CCG GCT
Val Thr Asp Phe Ala Thr Asn Ile Trp Leu Gln Met Glu Asp Leu Gly Ala Ala Pro Ala 450                                   480
GTT CAG CCG ACT CAG GGC GCT ATG CCT ACC TTC ACC TCT GCT TTC CAG CGT CGT GCT GGT
Val Gln Pro Thr Gln Gly Ala Met Pro Thr Phe Thr Ser Ala Phe Gln Arg Arg Ala Gly 510                                   540
GGT GTT CTG GTA GCT TCT CAG CTG CAC CGT TTC CTC GAG CTG GCT TAC CGT GGT CTG CGT
Gly Val Leu Val Ala Ser Gln Leu His Arg Phe Leu Glu Leu Ala Tyr Arg Gly Leu Arg TAC CTG GCT GAA CCG TAA TAG AAT TC
Tyr Leu Ala Glu Pro End End

FIG.7
```

DAYS OF STUDY

METHOD FOR PURIFYING GRANULOCYTE COLONY STIMULATING FACTOR

This application is a divisional of application Ser. No. 08/383,533, filed Feb. 1, 1995, now abandoned, which is a continuation of application Ser. No. 08/013,134, filed Feb. 3, 1993, which is a continuation of application Ser. No. 07/348,011, filed May 9, 1989, now abandoned, which is a continuation-in-part of application Ser. No. 07/193,857, filed May 13, 1988, now abandoned, all of which are hereby incorporated by reference herein, including the drawings.

FIELD OF THE INVENTION

The present invention is directed to the use of granulocyte colony stimulating factor (G-CSF) to treat or prevent infections in animals. More specifically, the invention is directed to the use of G-CSF, in particular, human G-CSF (hG-CSF) or bovine G-CSF (bG-CSF), in treating or preventing infections. The source of the G-CSF may be naturally derived or may be derived from genetically engineered prokaryotic or eukaryotic host cells containing recombinant plasmid or viral DNA vectors carrying the human or bovine G-CSF gene, or genetically engineered variants of human or bovine G-CSF genes, or synthetic human or bovine G-CSF genes. The present invention is also directed to DNA gene segments, biologically functional recombinant plasmids and viral DNA vectors, and prokaryotic and eukaryotic host cells containing such recombinant plasmids and vectors, all of which contain a bovine G-CSF gene or a genetically engineered variant of a bovine G-CSF gene.

BACKGROUND OF THE INVENTION

Infections in animals result in losses of billions of dollars per year in the meat and dairy industries. Although antibiotic therapy is now used for animal infections with some success, huge losses persist. Examples of such infections are mastitis in cows, and shipping fever in cattle.

Bovine Animals

A. Mastitis

The most costly problem in dairying today is mastitis. Mastitis is defined as an inflammation of the mammary gland. It may affect any mammal, for example cows, ewes, and goats, but bovine mastitis is of the greatest economic importance. Bovine mastitis is an infection of the udder of ruminants such as cows, mainly caused by gram positive and gram negative bacteria and especially in cows in intensive milk producing units. The bacterial infection results in the inflammation of the mammary gland (i.e. teats and udder). The disease is particularly troublesome and of considerable economic importance because the pathogen is readily transferred from one animal to another during the milking process. Some of the main pathogenic microorganisms causing bovine mastitis are *Staphylococcus aureus, Streptococcus agalactiae, Streptococcus uberis, Streptococcus dysgalactiae, Escherichia coli, Aerobacter aerogenes, Klebsiella pneumoniae,* and *Pseudomonas aeruginosa.* See also *Bovine Mastitis,* edited by Glenys Bloomfield, V&O Publications 1987, hereby incorporated by reference. These microorganisms invade the udder through the teat canal and produce inflammation of the milk-producing tissue causing the formation of scar tissue which, once formed, may cause a permanent reduction in the cowls milk production. An infection can also alter the composition, quantity, appearance and quality of the milk.

There are a variety of forms or types of bovine mastitis, with varying severity and symptomatology, including the following:

(1) Udder infection: The invasion of the udder cavity by microorganisms that multiply within the gland and cause inflammation;

(2) Nonclinical or subclinical mastitis; A form of mastitis in which there is no swelling of the gland or observable abnormality of the milk, although there are changes in the milk that can be detected by special tests. This type of mastitis is by far the most prevalent and causes the greatest overall loss in most herds. It often is referred to as "hidden" mastitis;

(3) Clinical mastitis; A form of mastitis in which the abnormal conditions of the udder and secretion are observable. Mild clinical mastitis involves changes in the milk such as flakes, clots, and a watery or unusual appearance. Heat and sensitiveness of the udder are slight or absent, but there may be signs of swelling. Severe clinical mastitis involves a sudden onset with swelling of the infected quarter which is hot, hard and sensitive. The milk appears abnormal and milk production drops. Sometimes, in addition to the local effects in the udder, the cow herself becomes sick. There are signs of fever, rapid pulse, depression, weakness and loss of appetite. The combination of these conditions often is referred to as acute systemic mastitis, because not only the udder, but the whole animal is affected; and (4) Chronic mastitis; A form of mastitis caused by a persistent udder infection that exists most of the time in the nonclinical form but occasionally can develop into an active clinical form. After these "flare-ups" the nonclinical form usually returns temporarily. (See generally *Current Concepts of Bovine Mastitis,* published by The National Mastitis Council, Inc., 2nd Ed. 1978 at p.5.)

Mastitis continues to cause large economic losses to the dairy industry. Mastitis affects the profitability of a herd in a number of ways, both directly and indirectly, including: (1) loss of milk production; (2) higher culling rates of infected cows; (3) decreased value of milk; (4) discarded milk following antibiotic treatment; (5) veterinary costs (antibiotics and veterinary visits); and (6) deaths. (*Bovine Mastitis,* Glenys Bloomfield, supra, at p.33.) An estimate of the yearly cost in the United States is $1 billion in milk alone. Treatment and culling costs raise this estimate of total costs to about $1.5 to $2 billion per year in the United States, and this represents the effect of mastitis on only 5% of the world dairy population. (*Current Concepts of Bovine Mastitis,* supra, at p.7.) While world figures are sketchy, projections from U.S.D.A. figures reveal a world-wide loss figure exceeding $20 billion annually.

Effective compounds to be used in the treatment or prevention of bovine mastitis should give the following results: (1) most or all of the above pathogens should be susceptible to the compound when the pathogen is in milk and other udder fluids; (2) the therapeutic effect should be relatively quick; (3) no significant irritation should be caused to the teats or udder of the cow, either by the active or other ingredients of the composition; and (4) the active compound should not stay in the milk for a period much in excess of the time required for the therapeutic activity so as to minimize the loss of milk, which has to be discarded as long as a foreign compound is present. There are other requirements for such a composition for the treatment of bovine mastitis but the above four criteria are some of the most important ones.

Antibiotic therapy has been a major component of mastitis control strategy. Table 1 summarizes a number of the antibiotics used in the treatment of mastitis:

TABLE 1

Antibacterial agents used in the treatment of mastitis

| Class | Compounds |
| --- | --- |
| 1. Beta-lactam antibiotics | |
| Penicillins | Ampicillin |
| | Cloxacillin |
| | Hetacillin |
| | Nafcillin |
| | Penicillin G |
| | (benzyl penicillin) |
| | Procaine penicillin |
| Cephalosporins | Cefoperazone** |
| | Cefuroxime* |
| | Cefalonium* |
| | Cefapirin |
| | Cefoxazole* |
| | Cefracetrile* |
| 2. Aminoglycoside antibiotics | Framycetin |
| | Neomycin |
| | Novobiocin |
| | Streptomycin |
| 3. Macrolide antibiotics | Erythromycin |
| 4. Tetracyclines | Chlortetracycline |
| | Oxytetracycline |
| 5. Polypeptide antibiotics | Polymyxin B |

*First generation;
**third generation Bovine Mastitis, supra, at p. 70.

Antibiotic treatment for mastitis is usually given by means of intramammary infusions, either in lactating cows when clinical mastitis is detected, or at drying off (dry cow therapy). (*Bovine Mastitis,* supra, at p.69.) In cases where severe clinical disease is present, antibiotics must be given parenterally (intramammary infusions are ineffective because of blockage of the ducts). (Ibid.)

The early hopes that antibiotics would allow complete control of the disease have not been realized. None of the above mentioned antibiotics utilized thus far has been entirely satisfactory. Additionally, it has been found to be very desirable to replace antibiotic treatment with treatment by non-antibiotic chemo-therapeutic drug compounds, for the following reasons:

(1) Antibiotics effective in human medicine should not be utilized in veterinary medicine, in order not to build up strain resistance of bacteria appearing in human diseases;

(2) Antibiotics should be reserved for such diseases for which no chemo-therapeutic drug compound would be available, as it has been proved that bacterial strains build up resistance to an antibiotic after extended use of such antibiotic; and (3) *Staphylococcus aureus,* one of the above-noted pathogens, has already built up a resistance against most of the antibiotics utilized in the treatment of bovine mastitis.

One such method for treatment by a non-antibiotic chemo-therapeutic drug compound is described in U.S. Pat. No. 4,610,993 which claims a method for treating animals for bovine mastitis with an effective amount of at least one pyridine-N-oxide disulfide compound. Another method by the same inventors is described in U.S. Pat. No. 4,401,666 which claims a method for treating animals for bovine mastitis with an effective amount of at least one metallic salt of pyridine 2-thione-N-oxide.

Despite these several published methods, it remains very important to find cost-effective methods utilizing non-antibiotic compounds which would substantially overcome the drawbacks of antibiotics used thus far and yet would be effective in treating and preventing mastitis.

B. Shipping Fever

Another common disease affecting the cattle industry is shipping fever (bovine respiratory disease). Respiratory diseases continue to be the major cause of disease loss in beef cattle. In a year-long study of diseases of 407,000 yearling feedlot cattle, respiratory tract diseases were responsible for about ¾ of the clinical diagnoses and about ⅔ of the necropsy diagnoses.

The term "shipping fever" is used to describe the respiratory disease complex observed in cattle 6 months of age or older after shipment either into feedlots or onto pasture. The stresses of weaning, castration, dehorning, fasting, overcrowding, exposure to infectious agents, diet changes, environmental temperature extremes, and other stressors combined with viral, bacterial, mycoplasmal, and/or chlamydial infections contribute to the shipping fever complex. Mixing calves from different farms and/or salebarns greatly facilitates exposure to infectious agents. Population mixing may be a more important predisposing factor to shipping fever than stressors, although disease can occur without mixing and stressors usually dramatically worsen respiratory disease. Attempts to reduce stress by weaning, castrating, dehorning, etc. and acclimating cattle to new diets days or weeks prior to shipment are sometimes successful (but may not be cost-effective) in reducing the incidence of shipping fever. Vaccination against some of the infectious agents involved in shipping fever is sometimes helpful, but vaccines are available and efficacious for only a few of the agents known to be involved in the disease complex.

It is generally recognized that the ultimate cause of death in most cases of shipping fever is a bacterial (usually pasteurella) pneumonia. *Pasteurella haemolytica,* particularly type 1A, is the most common bacterium isolated from cases of respiratory disease in North America. Attempts to experimentally reproduce bacterial pneumonia in cattle are usually unsuccessful without severe stress and predisposing damage to the respiratory tract. It is generally believed that during times of stress, viruses, mycoplasma, and/or chlamydia most often provide the initial damage to the respiratory tract which predisposes to severe bacterial infection and disease.

A typical clinical respiratory disease outbreak usually begins within hours or days of the cattle's arrival at the feedlot. Recently shipped cattle in the 300 to 500 pound weight range commonly have a 20 to 80% morbidity and 1 to 10% mortality, or more, to respiratory tract disease. When the serum of cattle is analyzed for a four-fold antibody rise (seroconversion) and the respiratory tract and its secretions subjected to microbiologic isolations, a myriad of etiologic agents can be identified. Many animals, those sick and those apparently healthy, can be shown to have undergone infection by one or more agents (respiratory tract disease is probably seldom due to only one infectious agent). Although bovine respiratory disease complex is recognized clinically in the feedlot after arrival, the infections giving rise to clinical disease probably start at the salebarns, where cattle are first assembled from different farms. See also *Bovine Respiratory Disease,* Loan, R. W. Texas A & M University Press, 1984, hereby incorporated by reference.

Porcine Animals

Respiratory diseases, particularly pneumonia cost the swine industry hundreds of millions of dollars annually. It is the No. 1 problem of the growing-finishing period which accounts for half of the pig's life. Some of the common pathogens involved with pneumonia are *Pasteurella*

*multocida, Mycoplasma hyopneumonia, Haemophilus (Activobacillus) pleuropneumoniar Streptococcus suis, Salmonella cholersuis, Bordetella bronchiseptica,* pseudorabies virus, and swine influenza virus.

*Haemophilus Actinobacillus pleuropneumoniae* is a major cause of pneumonia in pigs. The disease is distributed worldwide and is one of the most economically important diseases of swine. In 1985 respiratory diseases in pigs were estimated to have resulted in a $208 million loss to producers. Pleuropneumonia is the most feared respiratory disease because vaccines fail to prevent infections or prevent the occurrence of persistently infected carrier animals.

The economic impact of an acute outbreak of pleuropneumonia in an unexposed herd is apparent with death losses ranging from 0.4% to 24% and morbidity being between 8.5% and 40%. Treatment of the acute disease has relied on the use of antibiotics. The routine use of antibiotics is rapidly being limited due to public concerns and governmental pressures.

Detailed histomorphologic and bacteriologic studies of porcine pleuropneumonia reveal that i) early in the disease large numbers of neutrophils localize at the sight of the infection; ii) there is a relationship between the ability of the pigs to restrict the infection to the lung, thus preventing bacteremia, and survival; and iii) experimental depletion of circulating neutrophils results in a more severe disease.

Equine Animals

The first two weeks of life (neonatal period) is a time when severe illness or death losses occur in foals due to infection (septicemia). Neonatal septicema represents significant losses to the equine industry. In septicemic foals the neutrophil count is commonly very low (neutropenia) and this is one reason for the fatality rate of 60–75% with sepsis in the neonatal foal.

Problems secondary to gram negative sepsis such as bone and joint damage, enteritis, omphalophlebitis, respiratory disease and poor development also account for significant losses in the equine industry. Immunoglobulin levels have not correlated well with protection from infection with 20% of septicemic foals having double the recommended level of IgG (400 mg/dl). Even with the advent of intensive care of the critically ill septic foal the survival rate is only 25–40%. Neutrophil function has been determined to be substantially reduced in foals with colostrum deprivation. This combined with the frequent development of neutropenia with sepsis in the neonatal foal are important reasons for the high mortality and perhaps for the initiation of infection.

Granulocyte Colony Stimulating Factor

Granulocyte colony stimulating factor (G-CSF) is one of several glycoprotein growth factors known as colony stimulating factors (CSFs) because they support the proliferation of haemopoietic progenitor cells. G-CSF stimulates the proliferation of specifc bone marrow precursor cells and their differentiation into granulocytes. It is distinguished from other CSFs by its ability to both stimulate neutrophilic granulocyte colony formation in semi-solid agar and to induce terminal differentiation of murine myelomonocytic leukemic cells in vitro. Granulocyte Colony-Stimulating Factor is a potent stimulus for neutrophil proliferation and maturation in vivo (Cohen et al., Proc. Natl. Acad. Sci. 1987; 84: 2484–2488). G-CSF is also capable of inducing functional activation or "priming" or mature neutrophils in vitro (Weisbart, R. H., Gasson, C. G., and D. W. Golde. Annals of Internal Medicine 1989; 110:297–303). G-CSF has been shown to prime human granulocytes, and enhance superoxide release stimulated by the chemotactic peptide, N-formyl-methionyl-leucyl-phenalalanine (S. Kitagawa, et al., Biochem. Biophys. Res. Commun. 1987; 144:1143–1146, and C. F. Nathan, Blood 1989; 74:301–306), and activate human neutrophil IgA mediated phagocytosis (Weisbart, R. H., et al., Nature 1988; 332: 647–649).

Neutrophils are a critical component of host defense mechanisms against bacterial and fungal infections. G-CSF is capable of inducing an increase in the absolute number of circulating neutrophils and enhances neutrophil function.

The cDNA cloning and expression of recombinant human G-CSF has been described, and it has been confirmed that the recombinant G-CSF exhibits most, if not all, of the biological properties of the native molecule (Souza, L. et al. Science 232, 61–65 (1986)). Sequence analysis of the cDNA and genomic DNA clones has allowed the deduction of the amino acid sequence and reveals that the protein is 204 amino acids long with a signal sequence of 30 amino acids. The mature protein is 174 amino acids long and possesses no potential N-linked glycosylation sites but several possible sites for O-linked glycosylation.

The cloning and expression of cDNA encoding human G-CSF has been described by two groups (Nagata, S. et. al., Nature 319, 415–418 (1986); Souza, L. M. et al., Science 232, 61–65 (1986)). The first report of a G-CSF cDNA clone suggested that the mature protein was 177 amino acids in length. The authors reported that they had also identified a cDNA clone for G-CSF that coded for a protein that lacked a stretch of three amino acids. This shorter from of G-CSF cDNA expresses the expected G-CSF activity. The second report describes a cDNA sequence identical to this short form and makes no mention of other variants. Since these authors confirmed that the short cDNA expresses G-CSF with the expected profile of biological activity, it is probable that this is the important form of G-CSF and that the longer form is either a minor splicing variant or the result of a cloning artifact.

Matsumoto et al., in Infection and Immunity, Vol. 55, No. 11, p. 2715 (1987) discuss the protective effect of human G-CSF on microbial infection in neutropenic mice.

The following patent publications relate to G-CSF: WO-A-8703689, assigned to Kirin/Amgen describes hybridomas producing monoclonal antibodies specific for human G-CSF and their use in the purification of G-CSF; WO-A-8702060, assigned to Biogen, discloses human G-CSF like polypeptides and methods of producing them; U.S. Pat. No. 4,810,643 assigned to Amgen, discloses human G-CSF like polypeptides, sequences encoding them and methods of their production; and WO-A-8604605 and WO-A-8604506, both asigned to Chugai Seiyaku Kabushiki Kaisha, disclose a gene encoding human G-CSF and infection inhibitors containing human G-CSF.

It is an object of the subject invention to provide an improved method of treating and preventing infections in animals.

It is a further object of the subject invention to provide a method of treating and preventing mastitis and shipping fever in bovine animals.

It is a further object of the subject invention to provide a method of treating infections in animals without build up of strain resistance of bacteria.

A still further object of the invention is to provide a purified and isolated polypeptide having part or all of the primary structural confirmation and one or more of the biological properties of naturally occurring bovine G-CSF, and DNA sequences encoding such bovine G-CSF.

Other objects, features and characteristics of the present invention will become apparent upon consideration of the following description and the appended claims.

SUMMARY OF THE INVENTION

The present invention provides DNA sequences, biologically functional recombinant plasmids and viral DNA vectors, and prokaryotic and eukaryotic host cells containing such recombinant plasmids and vectors, all of which contain a bovine G-CSF gene or a genetically engineered variant of a bovine G-CSF gene. The invention also provides polypeptides encoded by the bovine G-CSF gene or variants thereof. A method for treating or preventing infections in animals is also disclosed.

Novel DNA sequences of the invention include sequences useful in securing expression in prokaryotic or eukaryotic host cells of polypeptide products having at least a part of the primary structural conformation and one or more of the biological properties of naturally occurring bovine granulocyte colony stimulating factor. DNA sequences of the invention are specifically seen to comprise: (a) the DNA sequence of the coding region of the mature protein, set forth in FIG. 2a or its complimentary strand; (b) a DNA sequence which hybridizes (under hybridization conditions such as illustrated herein or more stringent conditions) to the DNA sequence in FIG. 2a or to fragments thereof; and (c) a DNA sequence which, but for the degeneracy of the genetic code, would hybridize to the DNA sequence in FIG. 2a. Specifically comprehended in part (b) are DNA sequences encoding allelic variant forms of bovine G-CSF and/or encoding other mammalian species of granulocyte colony stimulating factor. Specifically comprehended by part (c) are manufactured DNA sequences encoding bovine G-CSF, fragments of bovine G-CSF and analogs of bovine G-CSF with DNA sequences incorporating codons facilitating translation of messenger RNA in microbial hosts. Such manufactured sequences may readily be constructed according to the methods of Alton, et al., PCT published application WO 83/04053.

A further embodiment of the invention relates to synthetic genes designed to allow for expression of bovine G-CSF in *E. coli.*

The invention also comprises a method for purifying G-CSF.

Also comprehended by the invention are pharmaceutical compositions comprising effective amounts of polypeptide products of the invention together with suitable diluents, adjuvants and/or carriers useful in animal therapy.

The subject invention also relates to a method for treating and preventing infections in animals such as bovine animals, by administering a therapeutically effective treating or preventing amount of granulocyte colony stimulating factor, advantageously G-CSF derived from the gene of the animal to be treated. In addition, the invention relates to a method of treating or preventing mastitis or shipping fever by administering a therapeutically effective treating or preventing amount of granulocyte colony stimulating factor.

BRIEF DESCRIPTION OF THE DRAWINGS

FIG. 2a illustrates the coding region of the mature protein of bovine G-CSF.

FIG. 2b is the amino acid sequence of the mature protein;

FIG. 3 is the genomic sequence of the human G-CSF;

FIG. 4 is the DNA sequence of a first bovine G-CSF synthetic gene (bG-CSF dna);

FIG. 5 illustrates the oligos used to construct the subunits of a further bovine G-CSF synthetic gene (bG-CSF dna4);

FIG. 6 shows the two subunits of the bovine G-CSF synthetic gene bG-CSF dna4;

FIG. 7 shows the amino acids coded by the bovine G-CSF synthetic gene bG-CSF dna4;

DETAILED DESCRIPTION OF THE INVENTION

Figure 1:
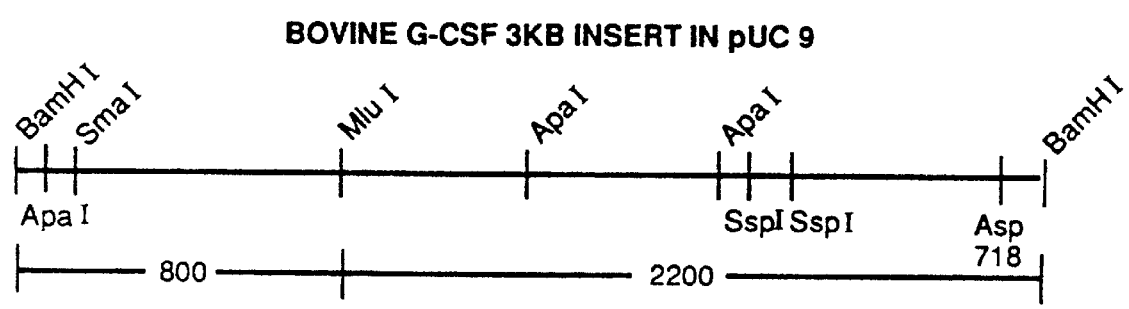
FIG. 1 shows the restriction map of bovine G-CSF.

A novel method for treating or preventing infections in animals has been discovered. Surprisingly it has been found that G-CSF is effective in a method of treating or preventing infections in animals, particularly mammals.

A variety of infections afflicting bovine animals, poultry, swine, horses, as well as dogs and cats, are treatable with G-CSF by the method of the subject invention.

Mastitis in bovine animals can be effectively treated with G-CSF. By "bovine animals" is meant a cow or ox. The subject invention also relates to treating or preventing diseases such as shipping fever in cattle by administration of G-CSF. "Mastitis" is an inflammatory disease of the mammary gland caused by a variety of pathogenic microorganisms, primarily gram-positive and gram-negative bacteria. A veterinarian of ordinary skill can readily determine whether an animal exhibits a mastitis infection. In one embodiment, the present invention relates to a method of treating or preventing infections such as mastitis in a non-human animal comprising administering a composition which comprises an effective amount of G-CSF.

The subject invention also relates to treating or preventing diseases in horses by administration of G-CSF. For example, neonatal septicema can be treated with G-CSF.

Increasing the number of circulating neutrophils in pigs during an acute outbreak of pleuropneumonia provides protection from infection and reduces the severity of the disease and the likelihood of persistent infections. G-CSF can be used to treat or prevent porcine infections such as pleuropneumonia.

By G-CSF is meant one of the hematopoietic growth factors known as granulocyte colony stimulating factors. The biological activities of G-CSFs include: stimulating the differentiation of a small number of progenitor "stem cells" into the variety of blood cell lines, stimulating the proliferation of those blood cell lines and stimulating the ultimate differentiation of mature blood cells from those lines. The preferred sources of the G-CSF polypeptide for treating or preventing mastitis are human and bovine, and may be naturally-derived or the product of genetically engineered host cells containing a DNA sequence encoding G-CSF.

The DNA encoding the G-CSF gene is a genomic DNA sequence, a cDNA sequence or a manufactured (or synthetic) DNA sequence which is expressed in a prokaryotic or eukaryotic host cell as a polypeptide having part or all of the primary structural conformation and one or more of the biological properties of naturally-occurring G-CSF. A biologically functional plasmid or viral DNA vector containing a DNA sequence encoding G-CSF may be used to transform or transfect a prokaryotic or eukaryotic host cell to produce cell lines expressing the G-CSF polypeptide, glycosylated or unglycosylated.

The various forms of human G-CSF, including their preparation and purification, useful in a method for treating or preventing mastitis are described in detail in U.S. Pat. No. 4,810,643, having a common assignee, which is hereby incorporated by reference. U.S. Pat. No. 4,810,643 describes and claims novel gene segments, biologically functional recombinant plasmids and viral DNA vectors and prokaryotic and eukaryotic host cells, which contain a G-CSF gene or a genetically engineered variant of a G-CSF gene. The host cells express biologically active G-CSF or a genetically engineered variant of G-CSF.

This application describes the isolation and characterization of a bovine G-CSF gene and in particular describes and claims novel gene segments, biologically functional recombinant plasmids and viral DNA vectors, and prokaryotic and eukaryotic host cells, which contain a bovine G-CSF gene or a genetically engineered variant of a bovine G-CSF gene. The host cells transformed or transfected with the recombinant plasmids or viral DNA vectors express biologically active bovine G-CSF or a genetically engineered variant of bovine G-CSF. The protein expressed is purified using the method described below or methods well known to those skilled in the art.

DNA sequences coding for all or a part of bovine G-CSF are provided. Such sequences include: the incorporation of codons "preferred" for expression by selected non-mammalian hosts (e.g. *E. coli* preferred codons, see Nucleic Acids Res. 1986 vol.14 (13) pp 5125–5143); the provision of sites for cleavage by restriction endonuclease enzymes; the provision of DNA sequences which reduce or eliminate secondary structure interactions which inhibit transcription and/or translation; and the provision of additional initial, terminal or intermediate DNA sequences which facilitate incorporation into expression vectors. The DNA sequences of the invention also include sequences having an optimized ribosome binding site, and sequences which enhance transcription, translation, and/or secretion of the protein product.

The present invention also provides DNA sequences coding for microbial expression of polypeptide analogs or derivatives of bovine G-CSF which differ from naturally-occurring forms in terms of the identity or location of one or more amino acid residues (i.e., deletion analogs containing less than all of the residues specified for bovine G-CSF; substitution analogs, wherein one or more residues specified are replaced by other residues; and in addition, analogs wherein one or more amino acid residues are added to a terminal or medial portion of the polypeptide) and which share some or all the properties of naturally-occurring forms.

Figure 3A:
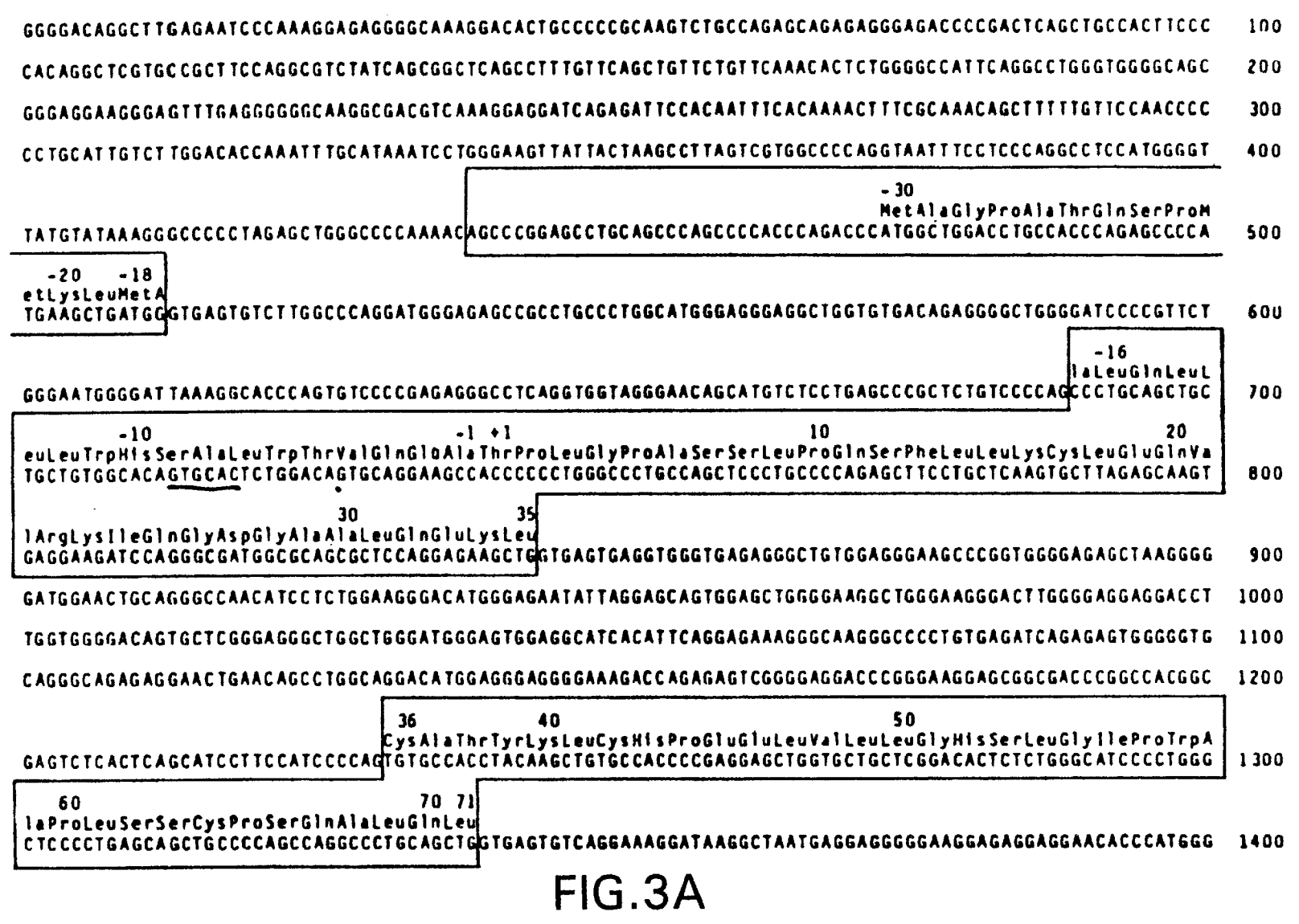
Figure 3B:
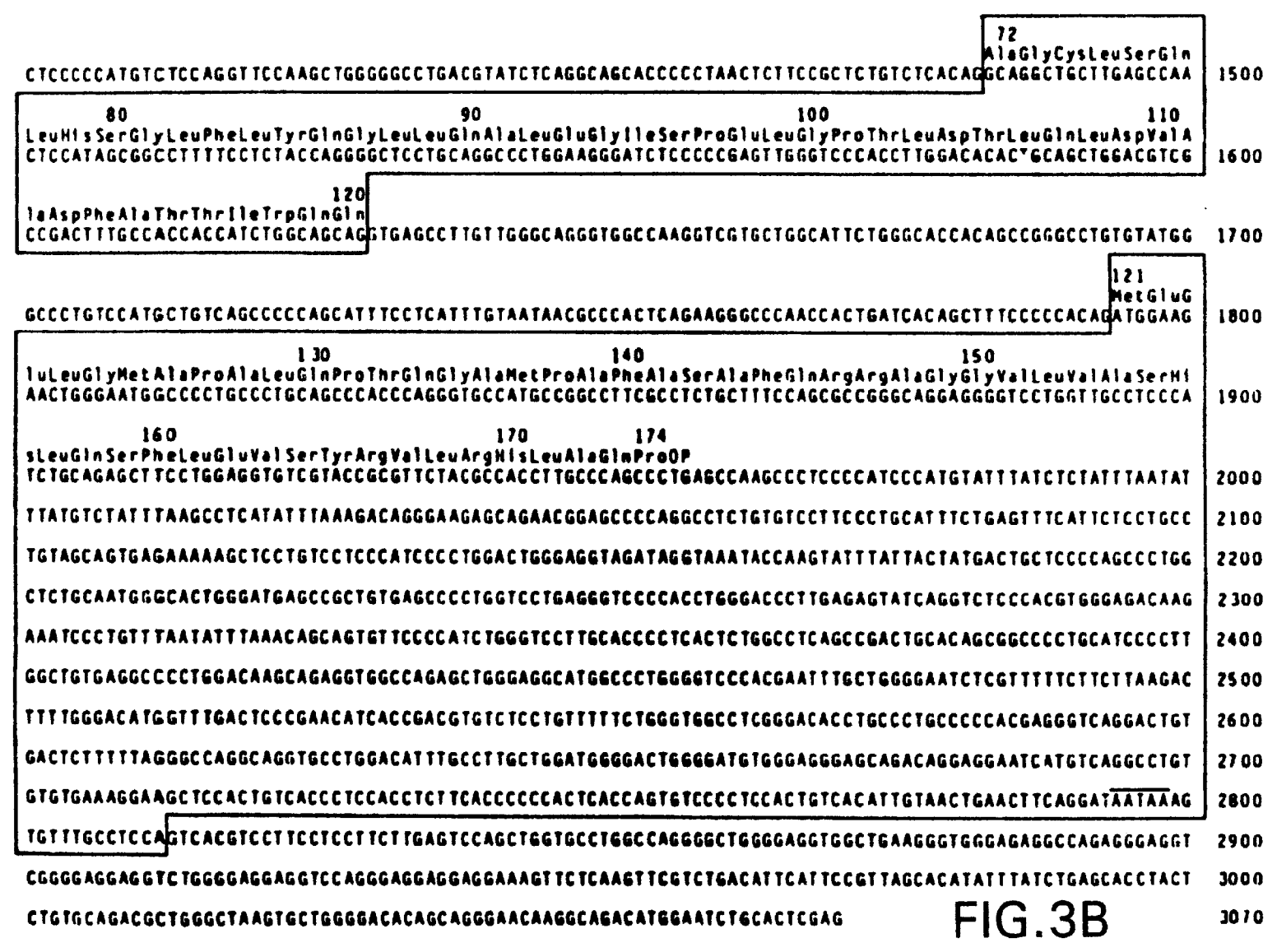

Also comprehended by the present invention is that class of polypeptide coded for by portions of the DNA complement to the top strand bovine CDNA or genomic DNA sequences of FIGS. 2a or 3 herein, i.e., "complementary inverted proteins" as described by Tramontano, et al., *Nucleic Acids Res.*, 12, 5049–5059 (1984).

The present invention relates to purified and isolated polypeptide products having part or all of the primary structural conformation (i.e., continuous sequence of amino acid residues) and one or more of the biological properties (e.g., immunological properties and in vitro biological activity) and physical properties (e.g., molecular weight) of naturally-occurring bovine G-CSF including allelic variants thereof. These polypeptide are also characterized by being the product of chemical synthetic procedures or of procaryotic or eukaryotic host expression (e.g., by bacterial, yeast, higher plant, insect and mammalian cells in culture) of exogenous DNA sequences obtained by genomic or cDNA cloning or by gene synthesis. The products of typical yeast (e.g., *Saccaromyces cerevisiae*) or prokaryote [e.g., [*Escherichia coli* (*E. coli*)]] host cells are free of association with any mammalian proteins. Depending upon the host employed, polypeptide of the invention is glycosylated with mammalian or other eukaryotic carbohydrates or is non-glycosylated. Polypeptides of the invention may also include an initial methionine amino acid residue (at position −1).

In addition to naturally-occurring allelic forms of bovine G-CSF, the present invention also embraces other bovine G-CSF products such as polypeptide analogs of bovine G-CSF and fragments of bovine G-CSF. All such forms of bovine G-CSF may be useful in the method for treating or preventing infections such as mastitis in animals. Following the procedures of the published application by Alton, et al. (WO/83/04053), hereby incorporated by reference, one can readily design and manufacture genes coding for microbial expression of polypeptides having primary conformations which differ from that herein specified for, in terms of the identity or location of one or more residues (e.g., substitutions, terminal and intermediate additions and deletions). Alternately, modifications of genomic and cDNA genes are readily accomplished by well-known site-directed mutagenesis techniques which generate analogs and derivatives of bovine G-CSF. Such products share at least one of the biological properties of bovine G-CSF but may differ in others. As examples, products of the invention include those which are foreshortened (e.g., by deletions); or those which are more stable to hydrolysis (and, therefore, have more pronounced or longer lasting effects than naturally-occurring); or which have been altered to delete one (or more) potential site(s) for n-linked or o-linked glycosylation (which result in higher activities for yeast-produced products); or which have one or more cysteine residues deleted or replaced (for example, by alanine or serine residues) and are more easily isolated in active form from microbial systems; or which have one or more tyrosine residues replaced by phenylalanine and bind more or less readily to G-CSF receptors on target cells. Also comprehended are polypeptide fragments duplicating only part of the continuous amino acid sequence or secondary conformations with bovine G-CSF, which fragments possess one activity of (e.g., receptor binding) and not others (e.g., colony growth stimulating activity).

According to another aspect of the present invention, the DNA sequence described herein which encodes bovine G-CSF polypeptides is valuable for the information which it provides concerning the amino acid sequence of this bovine protein (and similar mammalian proteins) which has heretofore been unavailable. The DNA sequences are also conspicuously valuable as products useful in effecting the large scale microbial synthesis of bovine G-CSF by a variety of recombinant techniques. Put another way, DNA sequences provided by the invention are useful in generating new and useful viral and plasmid DNA vectors, new and useful transformed and transfected prokaryotic and eukaryotic host cells (including bacterial, yeast, and mammalian cells grown in culture), and new and useful methods for cultured growth of such microbial host cells capable of expression of bovine G-CSF and G-CSF variants or analogs. DNA sequences of the invention are also conspicuously suitable materials for use as labelled probes in isolating bovine G-CSF and related protein encoding CDNA and genomic DNA sequences of other mammalian species. DNA sequences are also useful in various alternative methods of protein synthesis (e.g., in insect cells) or in genetic therapy in mammals. DNA sequences of the invention are useful in developing transgenic mammalian species which may serve as eukaryotic "hosts" for production of bovine G-CSF and bovine G-CSF products in quantity. (See generally Palmiter, et al., *Science,* 22(4625), 809–814 (1983))

Of applicability to bovine G-CSF fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. (See, e.g., Lerner, et al., *Cell,* 23: 309–310 (1981); Ross, et al., *Nature,* 294: 654–656 (1981); Walter, et al., *Proc. Natl. Acad. Sci. (USA),* 77: 5197–5200 (1980); Lerner, et al., *Proc. Natl. Acad. Sci. (USA),* 78: 4882–4886 (1981); Wong, et al., *Proc. Natl. Acad. Sci. (USA),* 78: 7412–7416 (1981); Green, et al., *Cell,* 28: 477–587 (1982); Nigg, et al., *Proc. Natl. Acad. Sci. (USA),* 79: 5322–5326 (1982); Baron, et al, *Cell,* 28: 395–404 (1982); Dreesman, et al., *Nature,* 295: 183–190 (1982); and Lerner, *Scientific American,* 248 (2): 66–74 (1983)). See, also, Kaiser, et al. *Science,* 223: 249–255 (1984) relating to biological and immunological activities of synthetic peptides which approximately share secondary structures of peptide hormones but may not share their primary structural conformation.

All of the above mentioned forms, fragments, variants and analogs of bovine G-CSF may be useful in the method of treating or preventing infections such as mastitis in animals as described herein.

In another embodiment of the invention, one or more additional colony stimulating factors are administered to the infected animal with G-CSF, egs. GM-CSF, M-CSF and multi-CSF (IL-3). The CSFs are administered together or separately. In a further embodiment, animal infections are treated by administering G-CSF with one or more of: the interferons (advantageously α-interferon), IL2, and TNF or, with traditional antibiotics such as penicillins, cephalosporins, and amino-glycosides.

This application also describes pharmaceutical compositions of G-CSF in a pharmaceutically acceptable carrier. These compositions may be administered intravascularly, intraperitoneally, subcutaneously, intramuscularly, or by intramammary infusion using forms known to the pharmaceutical art. For intravascular, intraperitoneal, subcutaneous, intramuscular or intramammary administration, active drug components may be combined with a suitable carrier such as water, saline, aqueous dextrose, and the like. Regardless of the route of administration selected, the compositions of the present invention are formulated into pharmaceutically acceptable dosage forms by conventional methods known to those skilled in the art. Advantageous formulations are described in commonly owned Ser. No. 285,159 hereby incorporated by reference. In one embodiment, sustained release formulations are used.

In another embodiment, G-CSF treatment is used in a prophylactic manner. G-CSF may be used as a prophylactic therapy to augment the host defense of animals who are at risk for acquiring a bacterial, yeast, or fungal infection. For example, G-CSF can be used as a prophylactic therapy in normal human patients at risk of acquiring pneumonia (e.g. nosocomial pneumonia), surgical wound infections, urinary tract infections, and intestinal infections. The term "normal" as used herein means an animal which has normal immune function and normal white blood cell count and differential. A description of the various nosocomial infections which the prophylactic therapy of the subject invention can be used against are stated in Nelson et al., J. Critical Illness, p12–24 (April 1988) hereby incorporated by reference. As a prophylactic G-CSF is administered typically 0–3 days before the event (e.g. surgery, vascular cannulation, catheter insertion, intubation) where there is a risk of infection. G-CSF is administered subcutaneously or intraventricularly daily in the dose range of 1 to 20 $\mu$g/kg, more advantageously, 3 to 15 $\mu$g/kg. A person skilled in the art will know how to adjust the dose.

In another embodiment, G-CSF is used to treat a patient immediately or soon, advantageously within eight hours, most advantageously within four hours after the patient has received a traumatic injury (e.g. human or animal bite, gunshot or knife wound or other puncture wound) requiring medical or surgical treatment. G-CSF is administered prior to detection (e.g. by standard microbiological or histological examination of the patient's tissues or body fluids) or clinical manifestation and symptoms (e.g. purulent exudate, chills, fever) of infection.

Cattle are treated prophylactically prior to shipping or other occurrences which may debilitate the cattle, in order to boost and prime their capacity to fight off infections. Administration of the G-CSF can be made at the time the cattle are processed, i.e. vaccinated, branded, etc. Treatment with G-CSF can also be made during dry cow therapy and/or just before a cow gives birth in order to reduce the likelihood of post partum intrauterine infections, and of mastitis during the early stages of lactation. See Kehrli et al., Am. J. Vet. Res., 50, No.2, 207 (1989) for a description of bovine neutrophil function during the periparturient period. Conventionally, there is no treatment with antibiotics just before birth because of residues which would appear in the cows milk making it unfit for use.

Several variables will be taken into account by the ordinary artisan in determining the concentration of G-CSF in the therapeutic formulations and dosages to be administered. Variables include administration route and condition of the animal.

Purification of G-CSF

G-CSF is produced in an insoluble form in *E. coli*. The purification procedure described below was developed to assure a monomeric, oxidized product. In order to accomplish this, the protein is solubilized in the presence of a denaturant and allowed to oxidize in the presence of this denaturant. The oxidized protein is then removed from the denaturant and purified to homogeneity. The following narrative describes the procedure for purifying human G-CSF with differences noted for the purification of bovine G-CSF.

Cell Lysis 350 g of frozen cell paste is combined with 2–3 liters of 1 mM dithiothreitol (DTT) and thoroughly dispersed. The cell suspension is then passed through a Gaulin homogenizer for a sufficient number of cycles to achieve greater than 95% breakage. The slurry is cooled to 5°±3° C. prior to homogenization and to below 18° C. beween cycles through the homogenizer. The homogenization slurry is centrifuged to recover the pellet, which contains >95% of the G-CSF originally present in the cell paste. (The bovine G-CSF breakage mixture contains no DTT).

Extraction

The homogenized pellet is next dispersed in about 3 liters of 1% deoxycholate (DOC), 5 mM DTT, 5 mM EDTA, 50 mM Tris, pH 9. This suspension is stirred at 15°–20° C. for 30–40 minutes and then centrifuged. (This DOC extraction step is not used for bovine G-CSF). The pellet is then resuspended in approximately 3 liters of cold water and recentrifuged. The G-CSF is recovered in the pellet with an overall yield of >80%. As an alternative to deoxycholate, another bile salt or non-ionic detergent is used.

Solubilization and Oxidation

The final pellet obtained from the above extractions is suspended in approximately 2.5 liters of 2% Sarkosyl, 40 mM Tris (pH 8.0) and allowed to solubilize at 15°–20° C. for 30 minutes. Copper sulfate is added to a final concentration of 40 $\mu$M, and the mixture is allowed to stir at least 12 hours at 15°–20° C. Approximately 70% of the G-CSF oxidizes into the correct monomeric form during this procedure.

Removal of Sarkosyl

The resultant solubilized protein mixture is centrifuged to remove insoluble debris and then diluted four-fold with 13.3 mM Tris, pH 7.7. About 2000 g of Dowex equilibrated in 20 mM Tris, pH 7.7 is then added. Dowex is an ion exchange resin. See *Dowex: Ion Exchange*, The Dow Chemical Company, Midland, Mich. (1988) hereby incorporated by reference. Advantageously, Dowex 1X4 20–50 mesh Type 1 is used, which is a strong base anion exchange resin, chloride form. This resin is a 4% crosslinked styrene-divinylbenzene polymer matrix with quaternary ammonium functional groups which serve as sites for ion exchange. "Type 1" means that the ammonium group is composed of a nitrogen atom bonded to a polymeric benzyl group, which is attached to the matrix, and three methyl groups. The mesh size is measured as wet resin on U.S. standard screen. The ammonium group is positively charged; this functionality will exchange its associated chloride ion for other negatively charged ionic species in a reversible reaction. Dowex 2 resin is a Type II resin in which one of the methyl groups is replaced by an ethanol group.

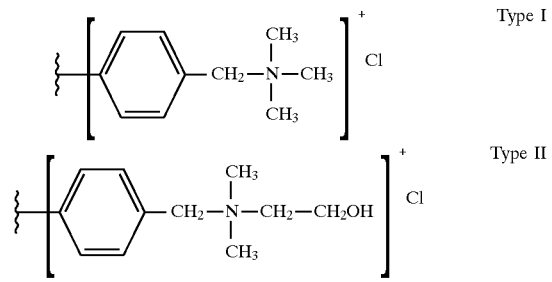

Type I and Type II resins differ primarily in their affinities for the hydroxide ion relative to other anions, and in chemical stability. Type II resins are more efficiently converted to the hydroxide form than Type I resins, but the Type I resins are inherently more stable chemically, especially in the hydroxide form.

The quaternary ammonium anion-exchange resins are highly ionized and can be used over the entire pH range. They are also capable of salt-splitting reactions, which convert a neutral salt to the corresponding base.

Other ion exchange resins which have strong anion exchange properties wherein the charge is inaccessible to the proteins of interest are alternatives to the use of Dowex in the subject invention.

This mixture is allowed to stir at least one hour at 15°–20° C. to remove Sarkosyl (N-Lauroylsarcosine sodium salt) (Sigma) from the protein solution,. and then the Dowex is filtered out. Greater than 80% of the correctly oxidized form of G-CSF can be recovered. (The bovine G-CSF is processed at 2°–8° C. during this step).

Anion Exchange Chromatography (This Step Not Used For Bovine G-CSF)

The resultant protein solution is applied to a DEAE-cellulose (Whatman DE-52 or equivalent) column equilibrated in 20 mM Tris, pH 7.7. The column is washed with 20 mM Tris, pH 7.7, until the absorbance at 280 nm of the eluant is approximately zero. The G-CSF is then eluted off the column with 20 mM Tris, 40 mM NaCl, pH7.7.

Cation Exchange Chromatography

The eluent from the DEAE column is adjusted to pH 5.4 with 50% acetic acid and diluted at least two-fold with 5 mM sodium acetate, pH 5.4. The solution is loaded onto a CM-Sepharose, fast flow column equilibrated in 20 mM sodium acetate, pH 5.4. After loading, the column is washed with 20 mM sodium acetate, pH 5.4, until the absorbance at 280 nm is approximately zero. The G-CSF is then eluted with 20 mM sodium acetate, 37.5 mM NaCl, pH 5.4. (The bovine G-CSF is eluted off at 150 mM NaCl in the same buffer).

The following examples are presented by way of illustration of the invention and are specifically directed to procedures carried out prior to identification of bovine G-CSF genomic and cDNA clones, to procedures resulting in such identification, and to the sequencing, development of expression systems based on genomic, CDNA and manufactured (or synthetic) genes and verification of expression of bovine G-CSF and analog products in such systems. The method of isolating the bovine G-CSF gene described below can also be used to isolate other animal G-CSF genes, which in turn can be used in producing other animal G-CSF. In addition, the examples illustrate methods for treating or preventing infections in animals, comprising administering an effective amount of G-CSF.

EXAMPLE 1

Screening a Genomic Library for the Bovine G-CSF Gene

In this example, a cDNA clone encoding human G-CSF as described in commonly owned U.S. Pat. No. 4,810,643 was used to screen for a genomic clone containing a bovine G-CSF gene. A phage (Charon 28) bovine genomic library prepared according to the procedure of Woychick, et. al., *Nucleic Acid Research* 10(22): 7197–7210 (1982) and obtained from J. Bloom and F. Rothman was plated out on *E. coli* strain K802 and screened using a nick translated probe consisting of a human G-CSF cDNA fragment isolated from HgiAI to StuI. A total of approximately $1.2 \times 10^6$ phage were plated on 12, 15 cm petri dishes, plaque lifted and hybridized to probe using the procedures described in Maniatus et al. *Molecular Cloning, A Laboratory Manual* (1982). A total of 7 positive clones were observed. Three clones yielding the strongest signals upon autoradiography in a secondary screening were grown in 1 liter cultures and phage DNA was prepared as described in Maniatus et al.

*Molecular Cloning, A Laboratory Manual* (1982). This DNA was mapped by restriction enzyme digestion and Southern blotting using the radiolabeled HgiAl to Stul probe. The mapping results showed that a BamHI fragment of about 3000 bases contained the entire G-CSF region. DNA from clone 2 was digested with BamHI to release an approximately 3000 bp bovine G-CSF containing fragment which was subsequently subcloned into pUC9 and further mapped by restriction endonuclease digests and Southern blotting.

A restriction endonuclease map (approximately 3.0 kb) of genomic DNA containing the bovine G-CSF gene is shown in FIG. 1. The sequence for the entire coding region of the mature bovine G-CSF was determined by subcloning fragments into M13 and sequencing them by the dideoxy method Sanger et al., *Proc. Natl. Acad. Sci. USA*, 74:5463 (1977). Sequences were confirmed or extended by utilizing internal primers off of the same clones. The sequence for the coding region was deduced by direct comparison with the human genomic G-CSF sequence (FIG. 3) and is shown in FIG. 2a. Splice juncture sites and amino terminal processing of the protein were assumed to occur at the same places as the human G-CSF. The DNA sequence codes for a mature protein of the same length as the human G-CSF (174 amino acids) and the proteins are 82% homologous.

EXAMPLE 2

Construction of Synthetic Bovine G-CSF Genes and Expression of Bovine G-CSF

This example relates to preparation of manufactured genes encoding bovine G-CSF and including *E. coli* preference codons, and to expression of bovine G-CSF.

Synthetic genes were designed to allow for the expression of bovine granulocyte colony stimulating factor (bG-CSF) in *E. coli* [bG-CSF dna (FIG. 4) and bG-CSF dna4 (FIGS. 5–7)]. bG-CSF is 174 amino acids in length and is 82% homologus to the human form of G-CSF (174 a.a.). The bovine protein contains five more charged residues (arg and glu) than does hG-CSF and is therefore believed to be more hydrophilic.

The genes bG-CSF dna (FIG. 4) and bG-CSF dna4 (FIGS. 5–7) were designed with maximum bias for *E. coli* codon preference. For gene bG-CSF dna, in addition to the coding sequence, an initiation ATG, a ribosome binding site, two termination codons, and a 5' Xbal and 3' BamHI restriction sites were included. The gene bG-CSF dna4 was also designed to have minimum secondary interactions and sufficient unique restriction sites for subunit assembly and gene manipulation. Unique BamHI and PstI sites were incorporated at positions identical to those found in the hG-CSF gene noted in commonly owned U.S. Pat. No. 4,810,643. This allows for generation of unique human/bovine hybrid genes and their protein products.

The gene was designed as two subunits (Subunit I Xbal-HindIII, and Subunit II HindIII-EcoRl) for cloning into sequencing/expression vectors (FIG. 6). Subunit I contains a short leader sequence with a Xbal cloning end and the ribosome binding site (RBS). Subunit II contains a pair of redundant stop codons and the EcoRl cloning end.

Briefly stated, the protocol employed was generally as set out in the disclosure of co-owned Alton, et al., PCT Publication No. WO83/04053, which is incorporated by reference herein. The genes were designed for initial assembly of component oligonucleotides (FIG. 5) into multiple duplexes which, in turn, were assembled into two discrete sections (FIG. 6). These sections were designed for ready amplification and, upon removal from the amplification system, could be assembled sequentially or through a multiple fragment ligation into a suitable expression vector.

Figure 16:
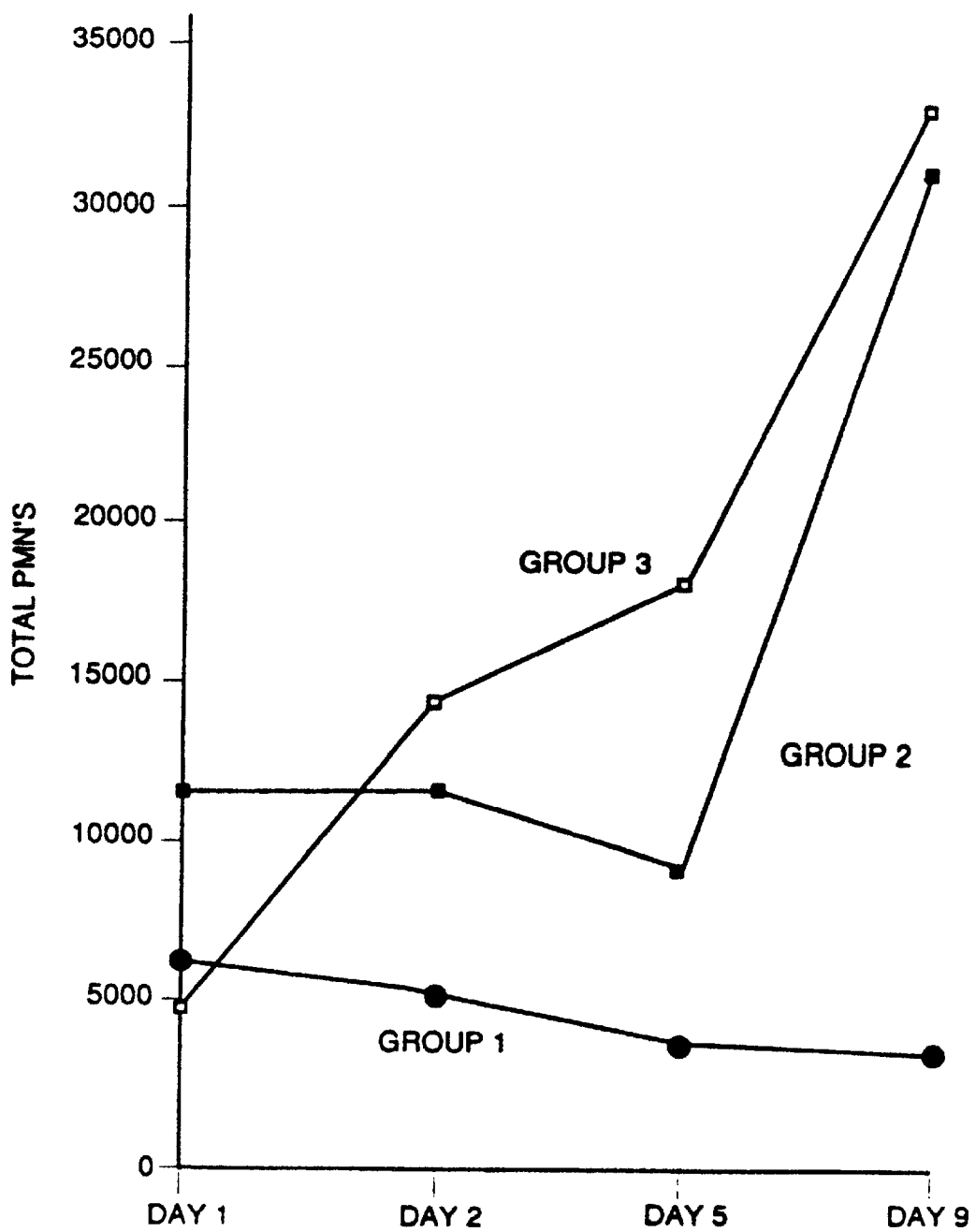

The construction of Sections I and II is illustrated in FIGS. 5 and 6. In the construction of Section I, as shown in FIGS. 5 and 6, 16 oligonucleotides were assembled into 8 duplexes. The 8 duplexes were then ligated to form Section I. It may also be noted in FIG. 6 that Section I includes an upstream Xbal sticky end and a downstream HindIII sticky end useful for ligation to amplification and expression vectors and for ligation to Section II.

Section II was constructed as shown in FIGS. 5 and 6. For this construction, 16 oligonucleotides were assembled into 8 duplexes. The 8 duplexes were then ligated to form Section II as depicted in FIG. 6. As also shown in FIG. 6, Section II includes an upstream HindIII sticky end and a downstream EcoRl sticky end useful for ligating into amplification and expression vectors, and to Section I.

Although any suitable vector may be employed to express this DNA, the expression plasmid pCFM1156 may readily be constructed from a plasmid pCFM836, the construction of which is described in published European Patent Application No. 136,490, and U.S. Pat. No. 4,710,473 both of which are hereby incorporated by reference. pCFM836 is first cut with Nde I and then blunt-ended with Pol I so that both existing Nde I sites are destroyed. Next, the vector is digested with Cla I and Sac II to remove an existing polylinker before ligation to a substitute polylinker. This substitute polylinker may be constructed according to the procedure of Alton, et al., supra. Control of expression in the pCFM1156 plasmid is by means of a lambda $P_L$ promoter, which itself may be under the control of a CI857 repressor gene (such as is provided in *E. coli* strain K12 Htrp or FM5). FM5 is described in Burnette et al. BIO/TECHNOLOGY Vol. 6, p699 (1988).

Section I was initially cloned into M13 from Xbal to HindIII and sequenced by the dideoxy method of Sanger et al., Proc. Natl. Acad. Sci. USA, 74:5463 (1977). Section II was cloned into M13 from HindIII to EcoRl and was also sequenced by the dideoxy method. Section I was cut out of M13 from Xbal to HindIII and Section II was cut out of M13 from HindIII to EcoRl. These two fragments were then ligated with pCFM1156 cut from Xbal to EcoRl and transformed into *E. coli* strain FM5 (or other suitable *E. coli* host cells known to those skilled in the art) to generate pCFM1156bG-CSF.

This plasmid contains the XpL promoter/operator region and has a temperature sensitive replicon. When *E. coli* strain, FM5, harboring pCFM1156bG-CSF is cultured at 28° C., the plasmid copy number is maintained at 10–20 copies/cell, and transcription from the λpL promoter is regulated by a temperature sensitive repressor. Growth at 42° C. results in an increased copy number and release of repression at the λpL promoter.

Recombinant bovine G-CSF begins to accumulate at elevated temperatures as the result of promoter activation and plasmid amplification. The λpL promoter lies just upstream from the ribosome binding site and the methionine initiation codon of bovine G-CSF. The transcription terminator, t-oop, lies just downstream from the two translational stop codons near the 3' end of the gene. Strains harboring the plasmid, pCFM1156bG-CSF, express r-metbG-CSF at up to 5% of the total cellular protein.

To increase the expression of bovine G-CSF, the synthetic gene was cloned out of pCFM1156bG-CSF into pCFM536 from Xbal to Kpnl to generate pCFM 536 bG-CSFl. This construction was transformed into FM5 and bovine G-CSF was expressed at up to 10% of the total protein. Using the oligonucleotide

TTA ATA ATG ATC CCA TTA GGT CCT GCA CGT TCT, site directed mutagenesis (see Example 3 for method) was performed to change the codons of the proline, leucine, and glycine at position 3, 4 and 5 from CCG, CTC, GGC to CCA, TTA and GGT. This new construction, pCFM 536 bG-CSF2, was transformed into FM5, and with this construction bovine G-CSF is expressed at up to 30% of the total protein.

E. coli Bovine G-CSF Purification

1. Cell Breakage and Sarkosyl Solubilization and Oxidation

About 100 grams of cell paste was weighed out and resuspended in 2.5 liters water. Cells were dispersed with a suitable mixer until completely dispersed. The suspension through the Gaulin Homogenizer four times at 8000 psig, keeping the temperature below 18° C. The homogenate was centrifuged in a Beckman J2-21 centrifuge using the JA-10 rotor at 10,000 rpm at 40 for thirty minutes.

The supernatant was decanted and discarded. The pellet was resuspended in 2.5 liters cold water and centrifuged in a J2-21 centrifuge using the JA-10 rotor at 10,000 rpm at 40 for thirty minutes. The supernatant was decanted and discarded. The pellets were resuspended in 380 ml of water, and 20 ml of 1M Tris pH 8, 100 ml 10% Sarkosyl, and 0.5 ml 1% copper sulfate pentahydrate were added. The mixture was stirred overnight at room temperature. The material was centrifuged in the J2-21 centrifuge using the JA-10 rotor for 30 minutes at 10,000 rpm at 40. The supernatant was decanted and saved. The pellets were discarded.

2. Dowex Removal of Sarkosyl

About 500 ml of cold water and 1 liter cold 20 mM Tris pH 8 plus 400 grams Dowex (equilibrated in 20 mM Tris, pH 8) were added to the supernatant. The mixture was stirred at 40 for 90 minutes. The slurry was filtered through a column and the flow through collected. The resin was washed with 400 ml 20 mM Tris pH 7.7 and this wash was added to the flow through yielding 2.4 liters. 3. CM-Sepharose Fast Flow Chromatography The pH of the material was adjusted to 5.4 using 50% acetic acid, and then centrifuged in the J2-21 centrifuge using the JA-10 rotor at 10,000 rpm at 40 for 25 minutes. The supernatant was decanted and saved. The pellet was discarded. The supernatant was loaded directly onto a 80 ml CM-Sepharose ion exchange column equilibrated in 20 mM sodium acetate pH 5.4. The column was washed with 100 mM NaCl in starting buffer and then eluted with 150 mM NaCl in starting buffer. Approximately 850 ml was collected of eluant containing bovine G-CSF.

4. Diafiltration

The 150 mM NaCl elution from the CM-Sepharose column material was adjusted to pH 3.5 with 0.1N HCl and then diafiltered using a tangential flow ultrafiltration device (Pellicon) equipped with 10,000 MW membranes against 0.35 mM HCl-Water, pH 3.5. The final volume was adjusted to yield bovine G-CSF at 2 mg/ml.

EXAMPLE 3

Construction of Bovine G-CSF Analogs

This example relates to the use of recombinant methods to general analogs of bovine G-CSF wherein the cysteine at position 17 was individually replaced by a serine.

Site directed mutagenesis procedures according to Souza, et al., published PCT Application No. WO85/00817, published Feb. 28, 1985, hereby incorporated by reference, were carried out using the oligonucleotide CTGCTGAAATC-CCTCGAACAG.

E. coli Bovine G-CSF Analog Purification

1. Cell Breakage and Urea Solubilization and Oxidation

About 100 grams of cell paste was weighed out and resuspended in 2.5 liters water. The cells were dispersed with a suitable mixer until completely dispersed. The suspension was passed through a Gaulin Homogenizer four times at 8000 psig keeping the temperature below 18° C. The homogenate was centrifuged in the J2-21 centrifuge using the JA-10 rotor at 10,000 rpm at 40 for thirty minutes. The supernatant was decanted and discarded. The pellets were resuspended in 2.5 liters cold water and centrifuged in the J2-21 centrifuge using the JA-10 rotor at 10,000 rpm at 4° for thirty minutes. The supernatant was decanted and discarded. The pellets were resuspended in 120 ml water and 40 ml 1M Tris pH 8.5 and 640 ml 10M Urea were added. The mixture was stirred 2–3 hours at room temperature, and then diluted 1:10 with 20 mM Tris pH 8.5. The mixture was then stirred overnight at room temperature. The material was centrifuged in the Beckman J6-B centrifuge with a JS 4.2 rotor at 4200 rpm at 4° for 45 minutes. The supernatant was decanted and saved. The pellets were discarded. The supernatant was adjusted to pH 5.4 with 50% acetic acid and the material was centrifuged in the J6B using the JS 4.2 rotor at 4200 rpm 4° for 45 minutes. The supernatant was decanted and saved. The mixture was then loaded directly onto a 100 ml CM-Sepharose ion exchange column equilibrated in 20 mM sodium acetate pH 5.4. The column was washed with 100 mM NaCl in starting buffer then eluted with 150 mM NaCl in starting buffer. Approximately 775 ml of eluant containing bovine G-CSF was collected.

2. Diafiltration

The 150 mM NaCl elution from the CM-Sepharose column material was adjusted to pH 3.5 with 0.1N HCl and then diafiltered using a tangential flow ultrafiltration device (Pellicon) equipped with 10,000 MW membranes against 0.35 mM HCl-Water, pH 3.5. The final volume was adjusted to yield bovine G-CSF at 2 mg/ml.

EXAMPLE 4

Method of Treatment of Infection by *Pasteurella Hemolytica*

A G-CSF study was run in cattle challenged with *Pasteurella hemolytica*. Calves weighing approximately 60 Kg were split into two groups of eleven. Both groups received 5 ml of bacteria ($3 \times 10^7$/ml) intratracheally on day 1. Four hours prior to challenge, the calves were treated with a weak solution (pH≈5.5) of acetic acid via transtracheal administration. The group receiving subcutaneously-administered human G-CSF (10 µg/Kg) had been pretreated for 4 days prior to infection and were treated daily for the remaining 9 days in the study.

Figure 8:
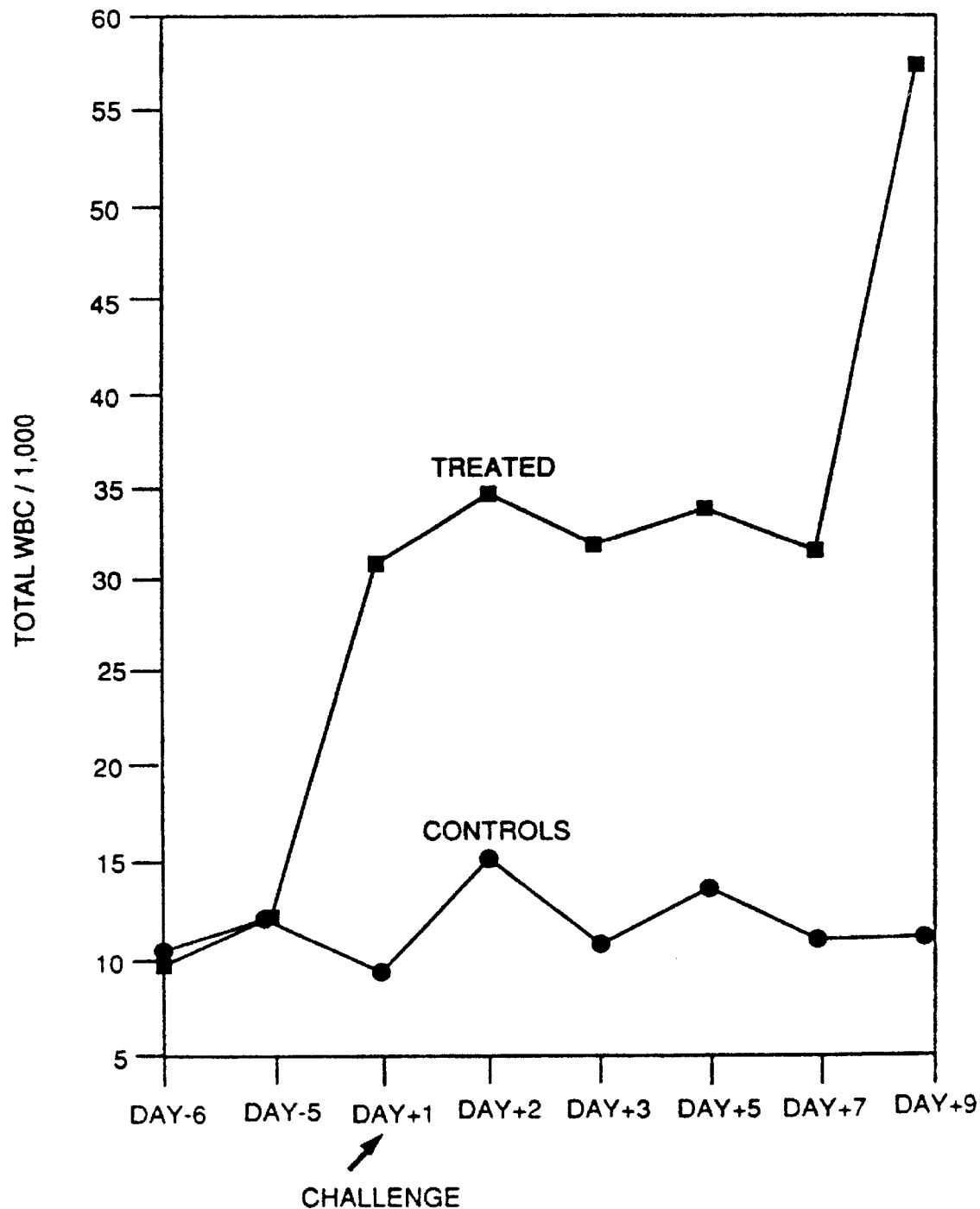
FIGS. 8–12 are graphic representations of the results obtained in Example 4 which relates to treatment of cows infected with *Pasteurella Hemolytica,* with G-CSF.
Figure 9:
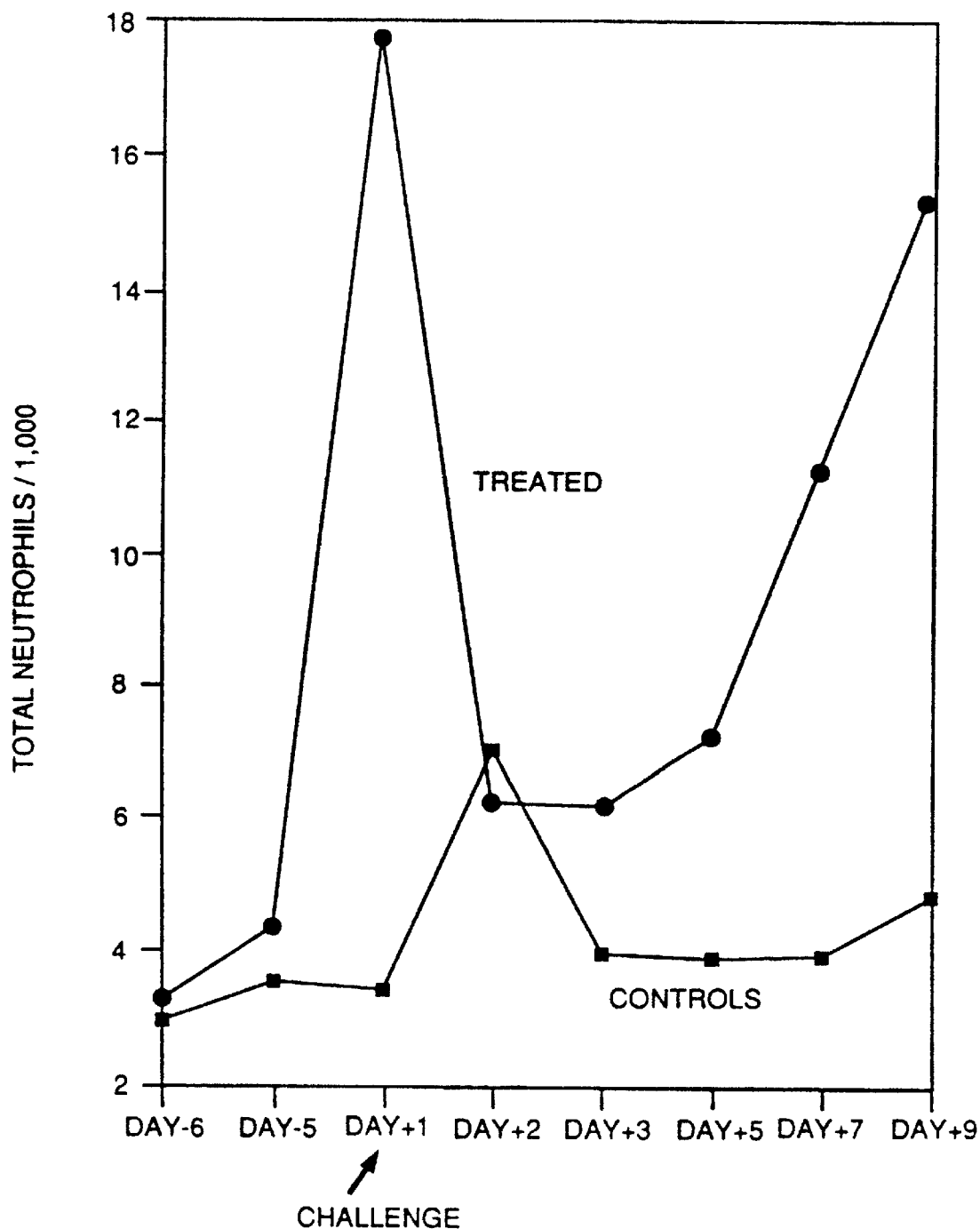
Figure 10:
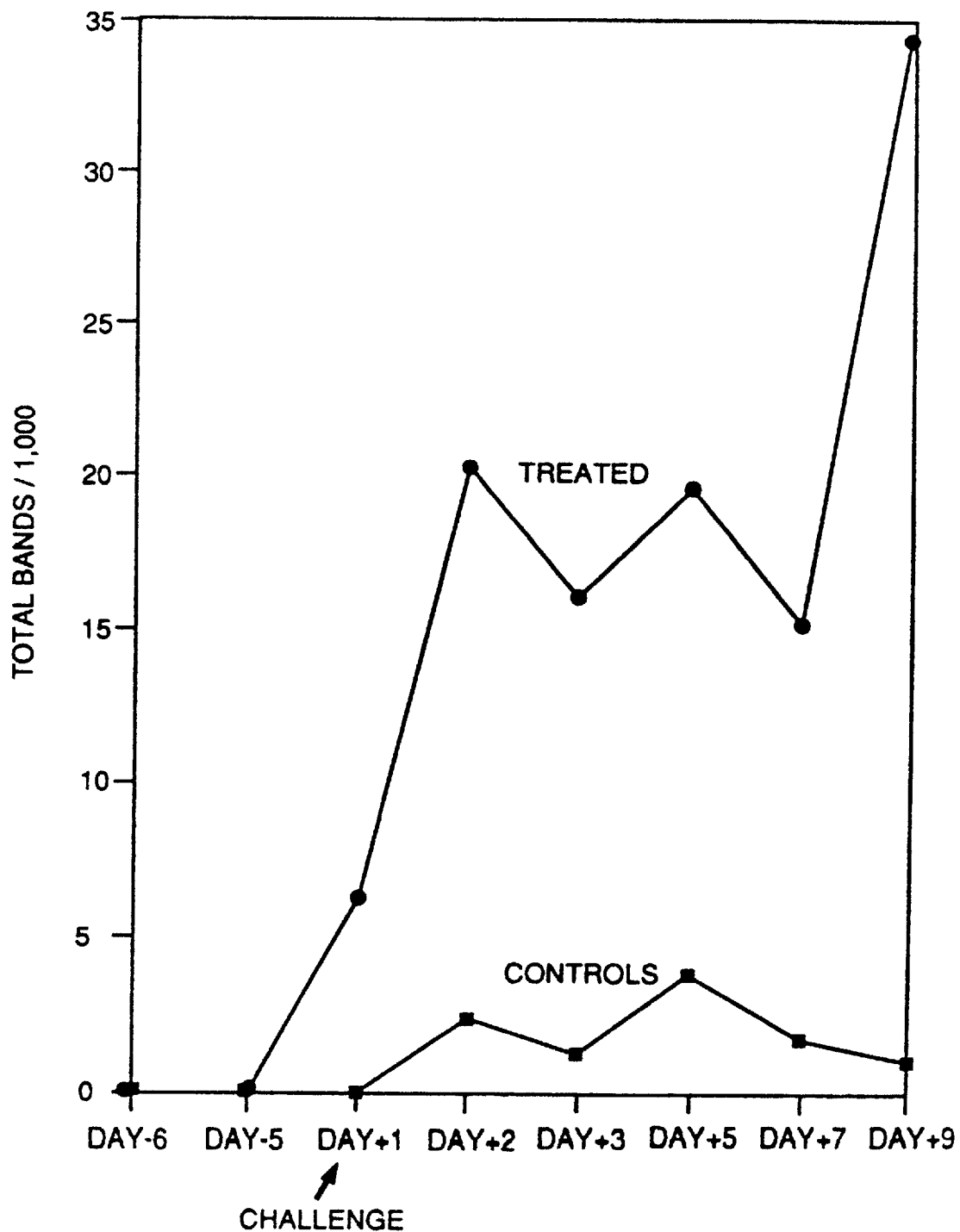
Figure 11:
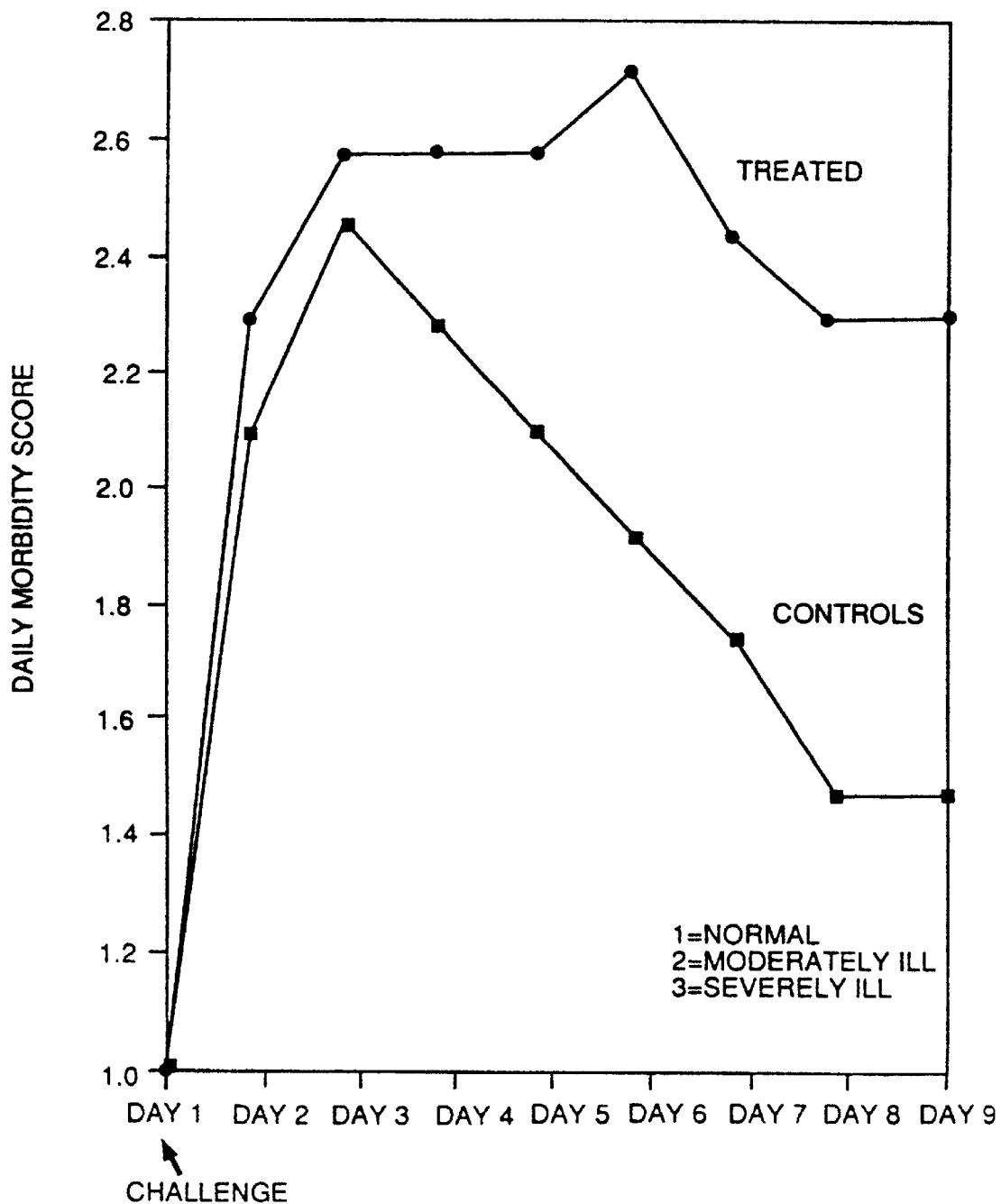
Figure 12:
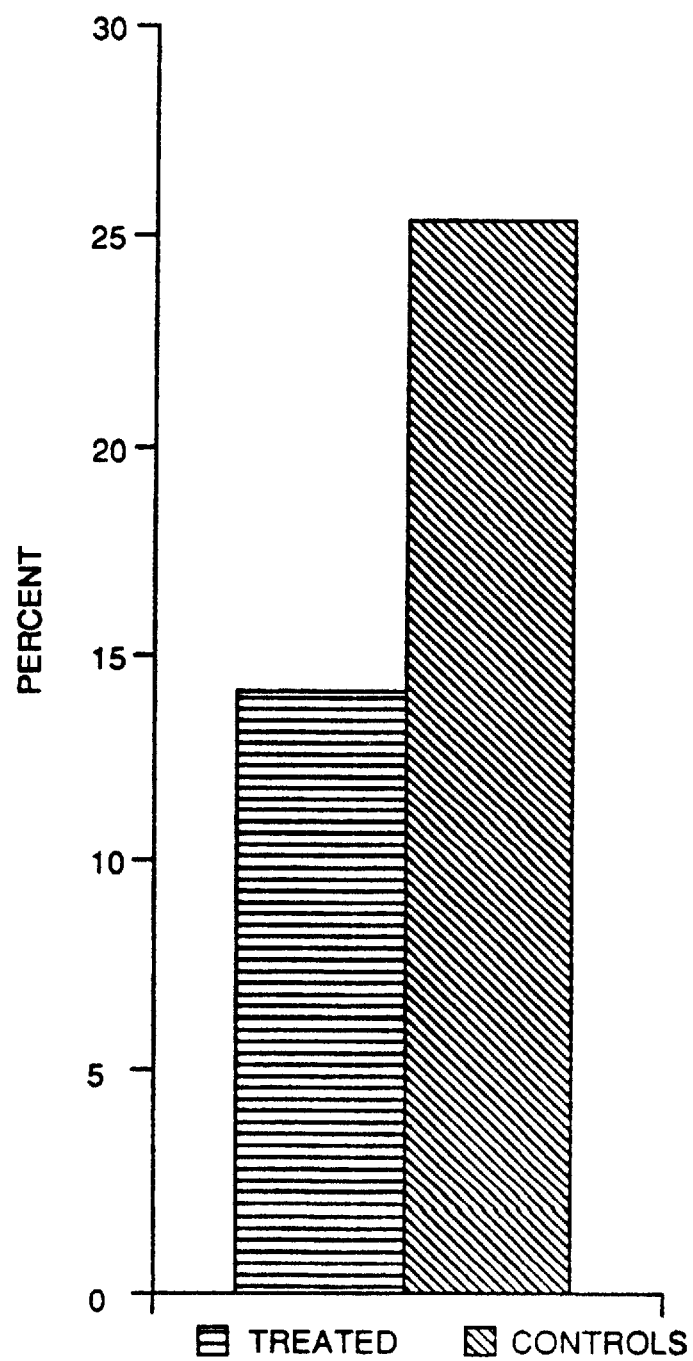

All cattle, except for one in the control group, showed clinical (subjective scoring) and histological signs of pneumonia. Although the G-CSF treated cattle were not protected against the infection, their clinical status at the end of the study was better than the control group, based not only on their clinical score but also on pathological scoring (%) of lung involvement. In addition, 3 cows in the control group died while none in the treated group died. FIG. 8 shows white blood cell count (WBC) as a function of time. FIG. 9 shows neutrophil count as a function of time. FIG. 10 illustrates band count as a function of time. Neutrophil count comprises the total of Segs (most mature neutrophils) and Bands (neutrophils slightly less mature than Segs). FIG. 11 shows morbidity as a function of time, and FIG. 12 shows percent lung involvement (percent by lung affected) versus time.

EXAMPLE 5

The Use of G-CSF as a Preventive/Therapeutic Agent for the Control of Bovine Respiratory Disease The purpose of this study was to determine the efficacy of human G-CSF in controlling bovine respiratory disease (BRD) caused by *Pasteurella haemolytica*. The groups were as follows (10 calves/group):

Group 1: Infected, unmedicated

Group 2: Infected, medicated (starting 5 days prior challenge)

Group 3: Infected, medicated (starting 12 hours prior to challenge)

Holstein bull calves at 1–2 days of age were purchased. The calves were placed in individual calf hutches and started on a diet of 1 gallon of milk divided twice per day. At 7 days of age free choice calf grain was offered, and at 7 days of age free choice water was offered.

Five days prior to challenge (day −5) all calves in group 2 received 10 μg/kg/calf of G-CSF administered SQ, SID. Twelve hours prior to challenge (day −½) calves in group 3 received 10 μg/kg/calf of G-CSF administered SQ, SID. Calves in group 1 received vehicle control starting at the time of challenge (day 0). Calves remained on medication until day 9 (day before termination of the study).

The medication was provided as 0.27 mg/ml solution and administered by injecting 10 μg/kg, SQ, SID. The vehicle control was administered by injecting 2 mls, SQ, SID.

Treatment levels were as follows:

Group 1: Vehicle control, Group 2: G-CSF 10 μg/kg, SQ, SID starting on day −5, Group 3: 10 μg/kg, SQ, SID.

The calves were challenged at 25 days of age (day 0). Four hours prior to challenge the calves were treated with a weak solution (pH~5.5) of acetic acid via transtracheal administration. Challenge with *Pasturella hemolytica* was by injecting 5 mls of a 1×10$^8$ overnight broth culture of the challenge organism. Calves were monitored for a total of 10 days.

Figure 13:
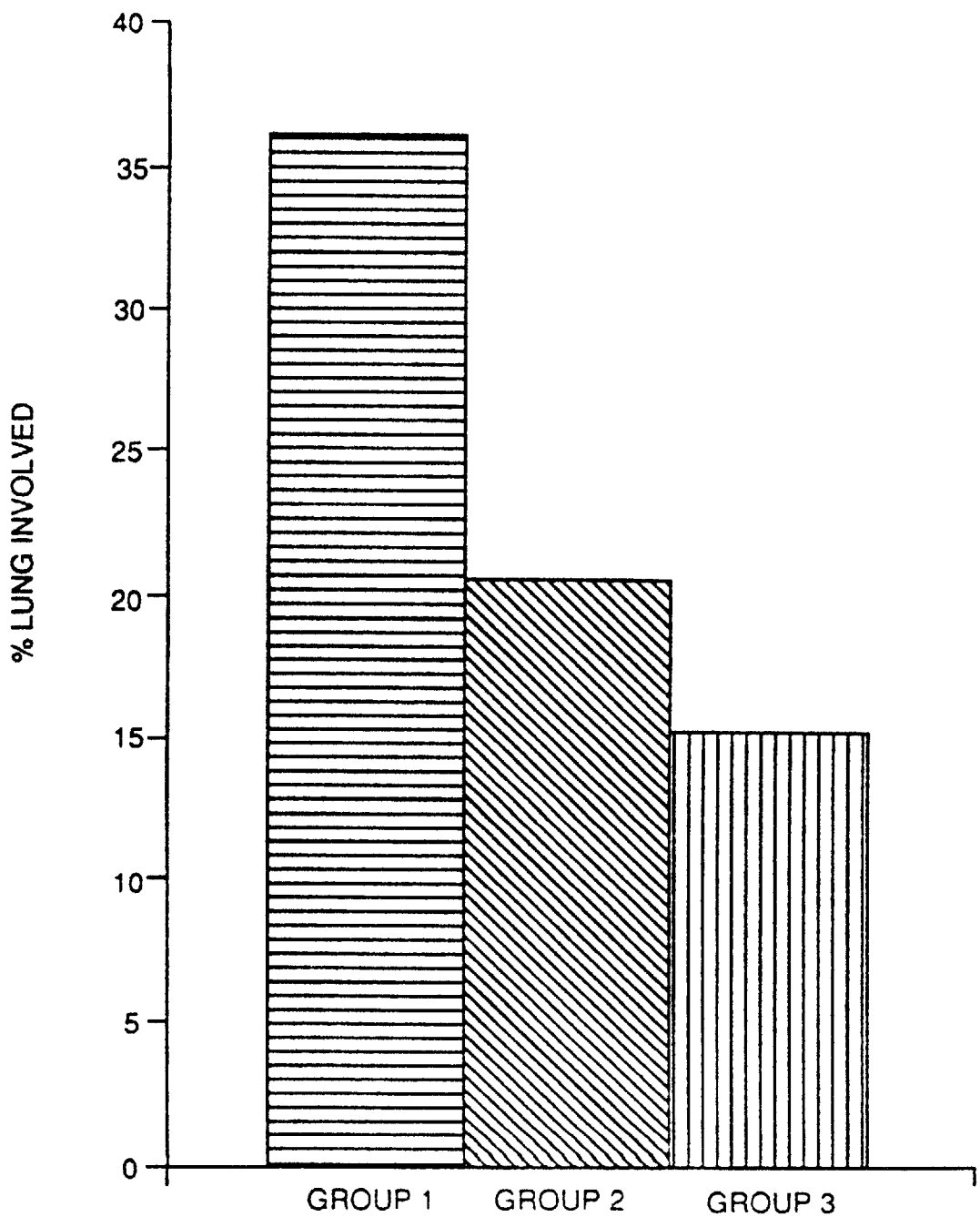
FIGS. 13–17 show the results obtained in Example 5 which relate to the use of G-CSF to control bovine respiratory disease.
Figure 14:
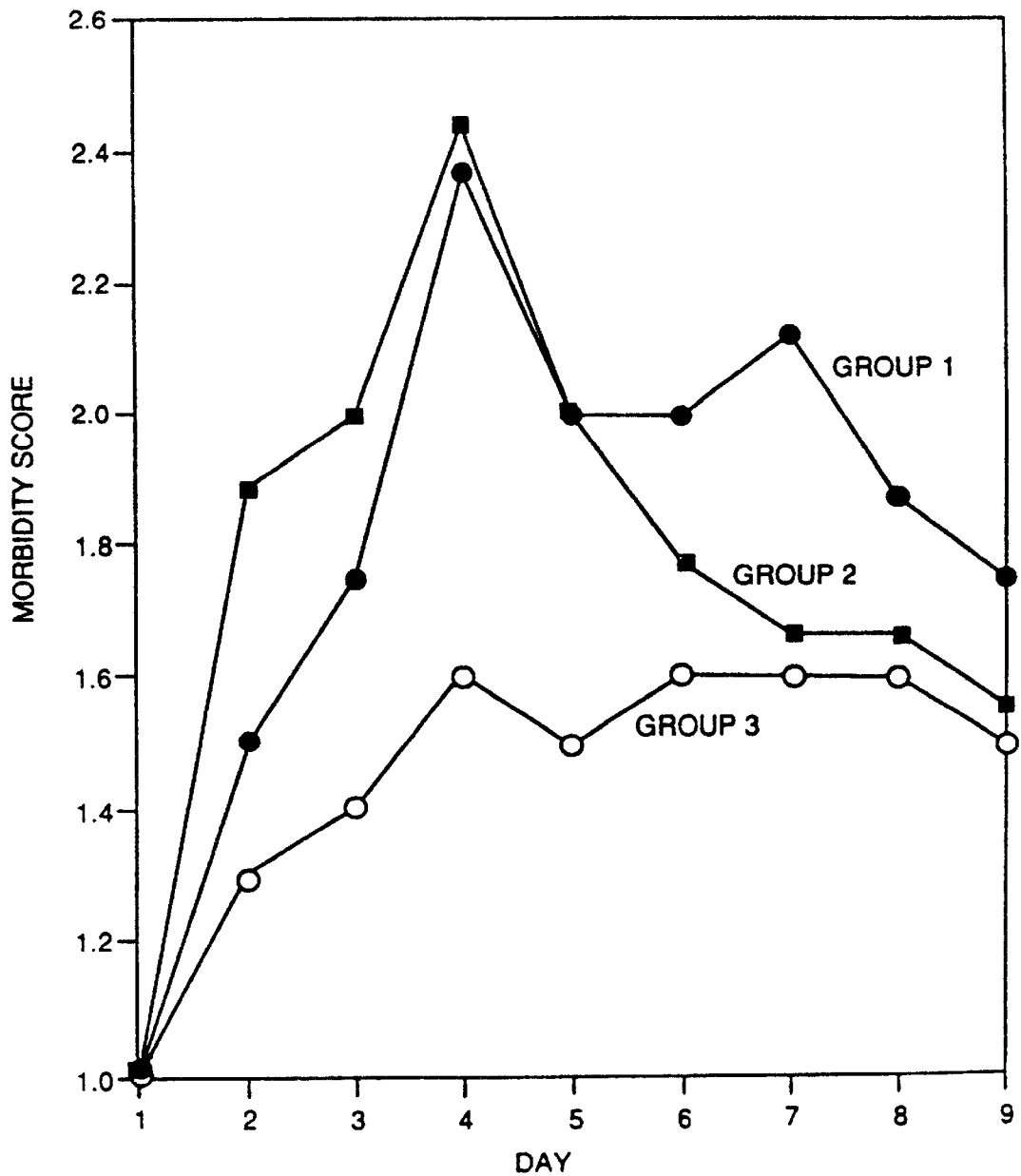
Figure 15:
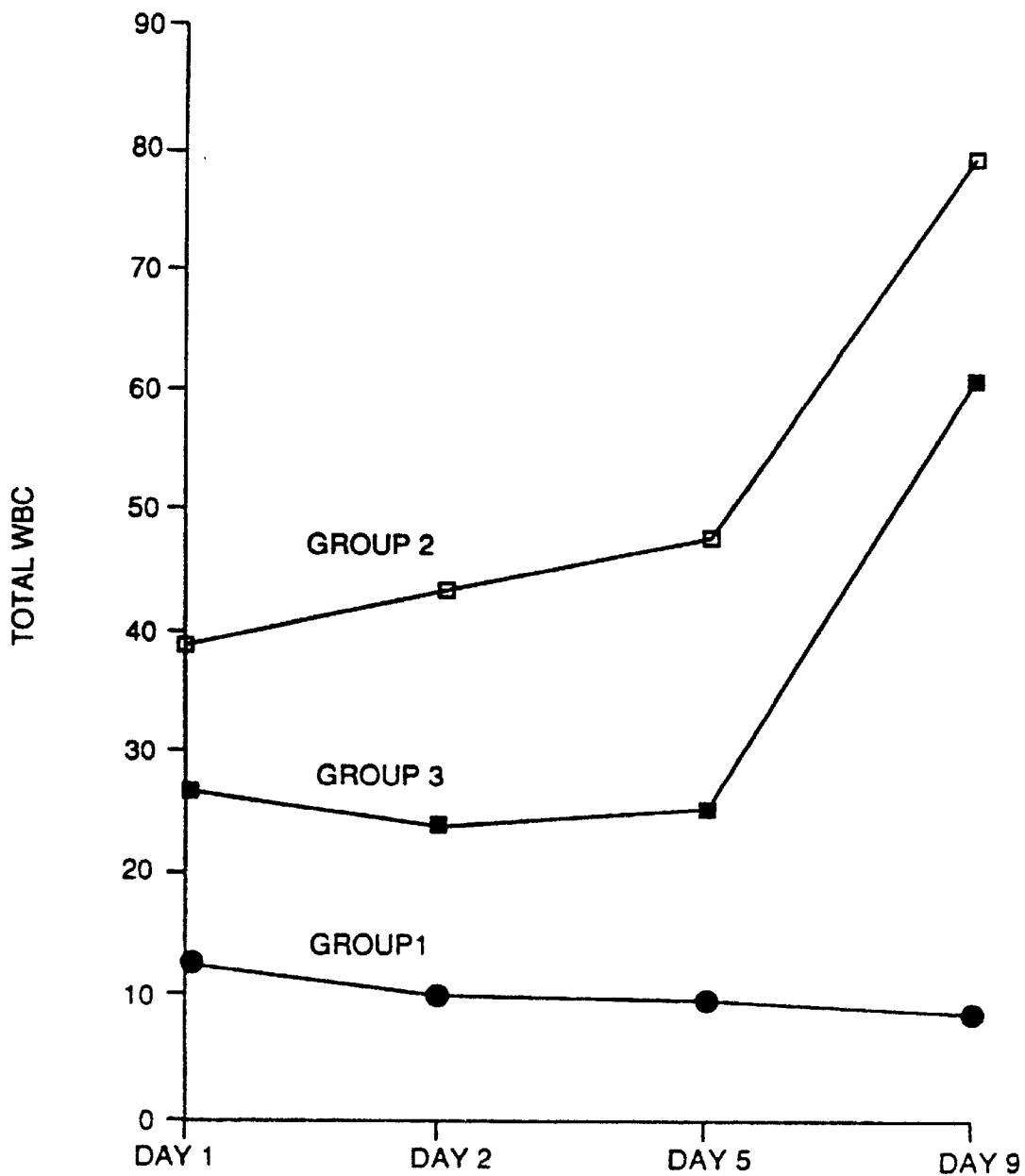
Figure 17:
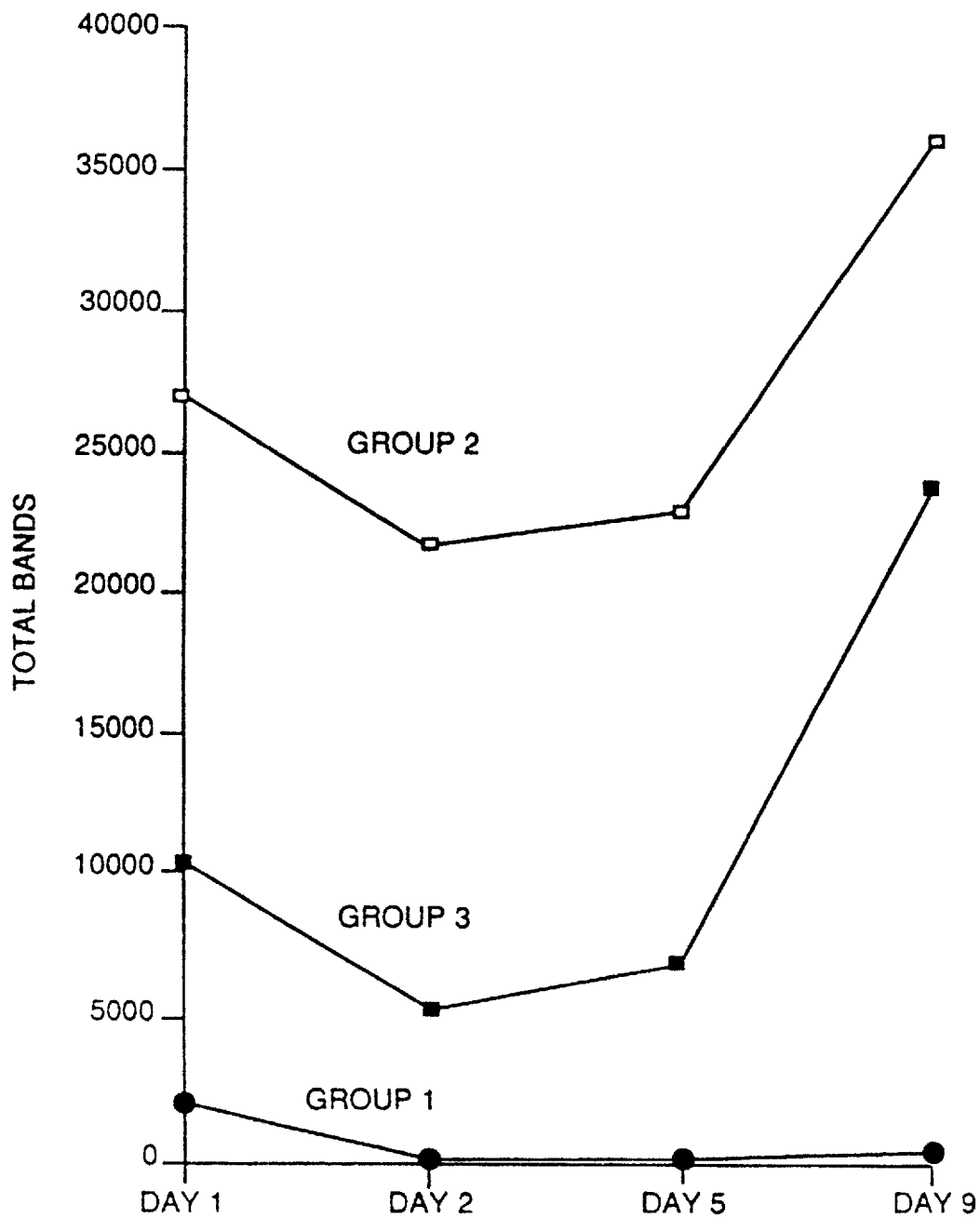

On day 10 the calves were euthanized and necropsied. The lungs were scored on the degree of involvement of pneumonia and cultured for bacteriology. FIG. 14 (see FIG. 13) shows the relative morbidity of the three groups. Morbidity was based upon body temperature, feed consumption and attitude. FIGS. 15, 16 and 17 illustrate WBC (white blood count), PMN (neutrophils) and bands versus time, respectively.

EXAMPLE 6

The Effects of G-CSF on the Incidence and Duration of Respiratory Disease and Immunological and Clinical pathological Parameters in Calves The purpose of this study was to determine the effect administering human G-CSF has on the incidence and duration of respiratory disease in calves. Parameters monitored included morbidity, mortality, complete blood counts and response to antigens and recall antigens. The study was conducted in a commercial calf barn.

Sixty (60) holstein bull calves, approximately 21 days of age, were purchased and placed in a calf barn over a 3 day period (day −3 through day −1). As the calves were placed in the barn they were assigned to one of two groups. The calves were placed in individual calf hutches in which there were 30 hutches in a row, with two rows and a 4 foot walkway between the rows. Calves were placed in an alternating manner. An even number of calves were placed each day. Calves were started on the study the day they were placed in the barn. Day 1 of the study occurred when the calf actually was placed in the barn. In other words, there were 3 day 1's, depending on the actual start day. All subsequent days were based on the actual start date.

Starting on day 1, calves in group 1 received daily injections of 10 μg/kg of body weight of G-CSF. Calves in group 2 received daily injections of a vehicle control. The injections continued for 21 consecutive days.

Starting on day 1 the calves were monitored daily for signs of respiratory disease by the animal health technician. The physical signs monitored were body temperature, appetite, respiratory rate and attitude. The monitoring continued for 30 consecutive days (day 1 through day 30). Any calf showing signs of respiratory disease (see diagnosis criteria below) was placed on therapy according to the treatment schedule noted below. All treatments were recorded. Any calf dying during the study was necropsied.

On days 1 (prior to start of injections), 7, 14, 21 and 28 all calves had blood taken for complete blood counts (CBC). In addition blood for CBC's was taken on the 1st and 4th day of respiratory disease. Tests run included packed cell volume (PCV), total red and white cell counts and a differential.

All calves becoming ill were started on therapy. The duration and type of therapy was recorded.

Comparisons were made between groups 1 and 2 for effects of G-CSF on complete blood counts, morbidity due to respiratory disease measured by daily observations and mortality.

RESPIRATORY DISEASE MONITORING CRITERIA

| RESPIRATORY DISEASE MONITORING CRITERIA | | |
|---|---|---|
| | NORMAL | ABNORMAL |
| BODY TEMPERATURE | <103.5 | >103.5 |
| APPETITE | 1 | 2, 3 & 4 |
| 1 = Drink entire amount of milk | | |
| 2 = Drink ¾ of milk | | |
| 3 = Drink ½ of milk | | |
| 4 = Drink <½ of milk | | |
| RESPIRATORY RATE | 1 | 2 & 3 |
| 1 = Normal | | |
| 2 = Slightly elevated | | |
| 3 = Extremely elevated | | |
| ATTITUDE | 1 | 2, 3 & 4 |
| 1 = Normal | | |
| 2 = Slightly depressed | | |
| 3 = Moderately depressed | | |
| 4 = Severely depressed | | |

Treatment Schedule

Treatment #1: 5 mg/lb oxytetracycline, IM. The duration of therapy was based on the response of the calf. Therapy continued for 2 days after parameters return to normal with a minimum of 4 days and a maximum of 8 days. If calves did not respond to treatment #1, they were started on treatment #2.

Treatment #2: 25mg/lb Sulfadimethoxine, PO, 1st day, 12.5 mg/lb 2nd and subsequent days. Maximum of 5 days.

Figure 18:
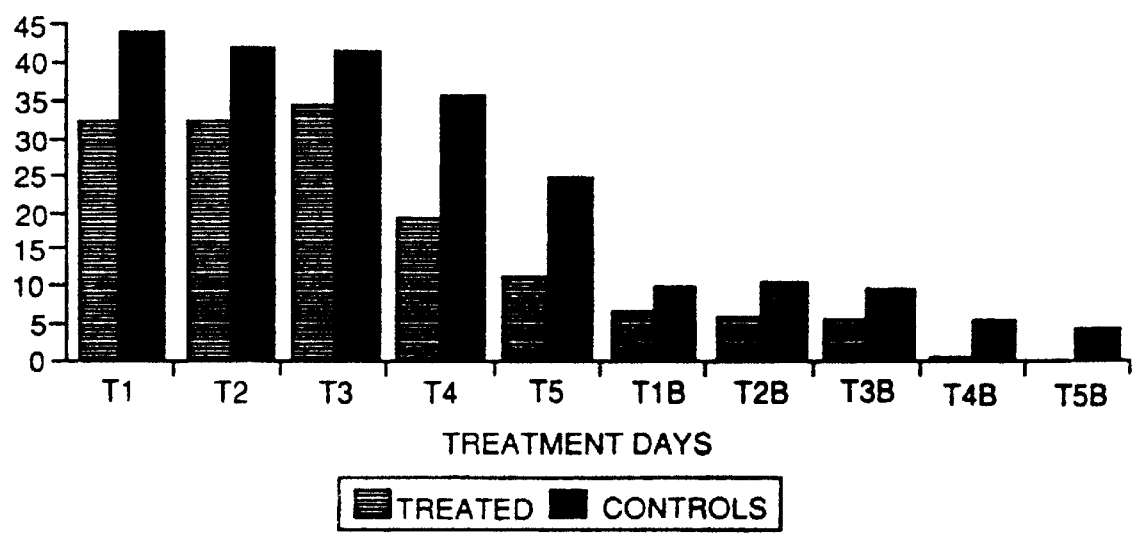
FIGS. 18–20 show results obtained in Example 6 which examine the effect of G-CSF on respiratory disease.

FIG. 18 illustrates the treatment days, for group 1 calves (receiving G-CSF), broken down by first day of treatment (T1), second day of treatment (T2), . . . first day of the second course of treatment (T1B), . . . fifth day of the second course of treatment (T5B). The treated group consistently has fewer number of total treatments for each treatment point. There is a slight trend to a greater difference between treated and controls as the number of treatments increases. For example, starting at T4, the difference between the treated and control calves increase to about a 40% improvement, compared to 15% at the earlier treatments.

Figure 19:
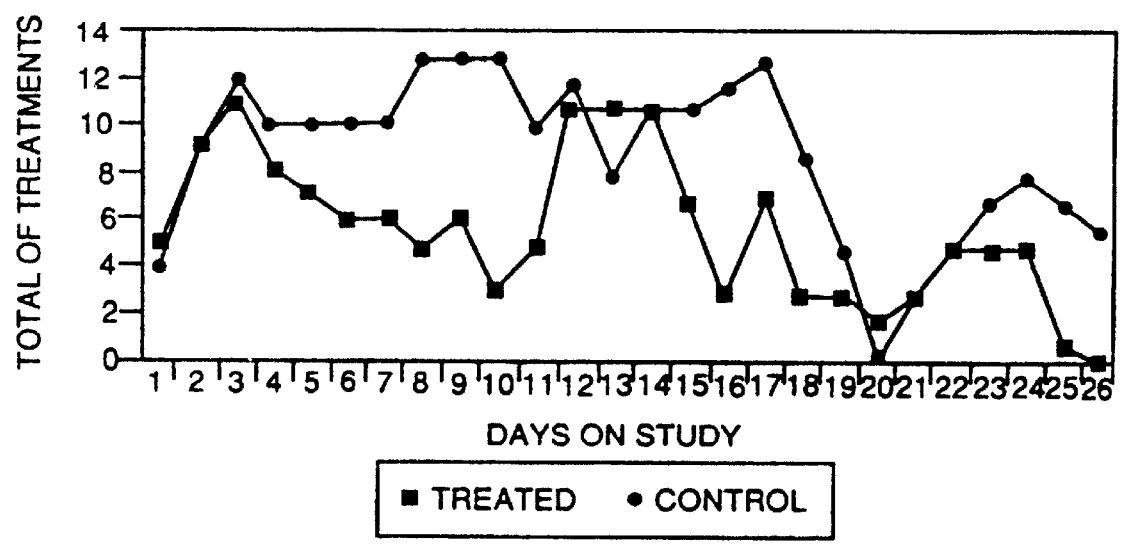

FIG. 19 illustrates the total number of treatments per day for the controls vs. the treated calves. Again this shows the reduction in treatments required for the treated calves vs. the controls. The improvement ranges from close to 50% at times, to 0%. The overall average % improvement for the treated calves is 36%.

Figure 20:
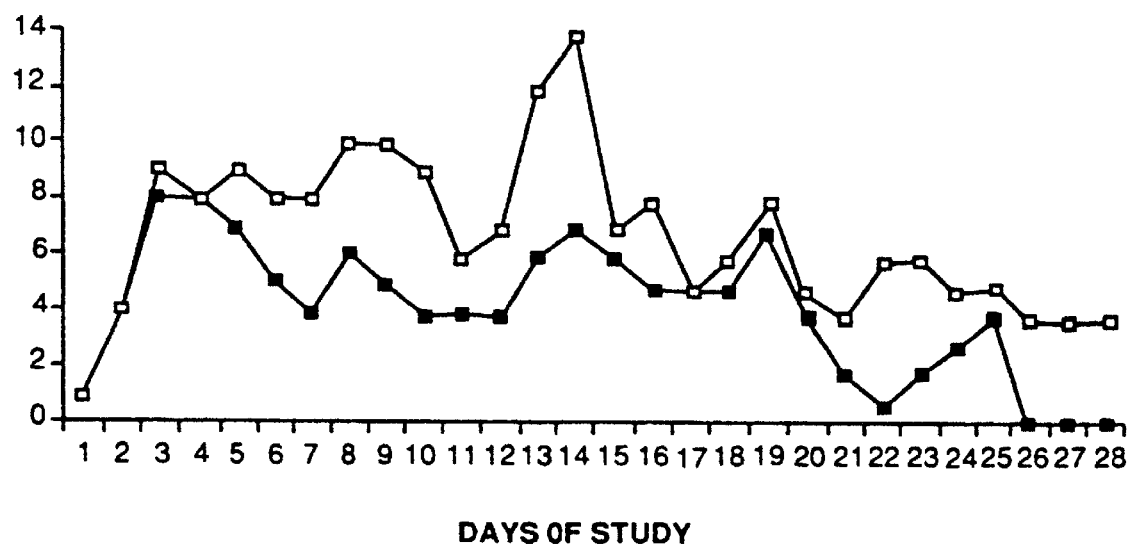

FIG. 20 illustrates the frequency of number of calves, by day, with temperatures above 103.5° F. The data corresponds very well with the total treatment days. There is a consistent improvement in temperatures for the treated calves vs. the controls. The percent improvement is basically the same as the total treatment days (39.9%).

G-CSF when administered to young veal calves prior to becoming infected with BRD and during infection significantly reduces the severity and length of the respiratory disease compared to placebo treated controls. G-CSF treated calves had less respiratory disease (27%) compared to controls, and they also became healthier sooner (47% improvement).

EXAMPLE 7

*Klebsiella Pneumonia*

The objective of this study was to determine if increasing the circulating neutrophil pool of cells would allow the dairy cow to respond in a more timely fashion upon bacterial challenge of the mammary gland.

G-CSF PROTOCOL:

1) The administration of the human G-CSF began two days after arrival and initial evaluation (PM milking) and continued to be given at the PM milking for a total of 15 days.
2) Dose/Route: 10.0 vg/kg daily via subcutaneous administration.
3) Control challenge group received 1.0 µg/kg G-CSF (daily) via subcutaneous administration for 8 days beginning on day 12.

MASTITIS CHALLENGE MODEL:

1) Organism: Klebsiella pneumoniae was given on the morning of the sixth day after the commencement of G-CSF administration.
2) Dose: 1.0 ml (approximately 200,000 CFU) administered aseptically via the streak canal into the left rear (D) quarter. The remainder of the quarters were used as controls.
3) No milk samples were taken for 3 hours after the challenge in order to allow for the bacteria to have time to establish in the quarter.
4) No antibiotic therapeutic intervention was used during the experiment with the exception of fluid therapy if required.

EXPERIMENTAL GROUPS:

Tx challenge (n=3) cow ear tag #: 736,924,964

Tx control (n=3) cow ear tag #: 248,293,790 control challenge (n=3) cow ear tag #: 124,771,4179

Figure 21:
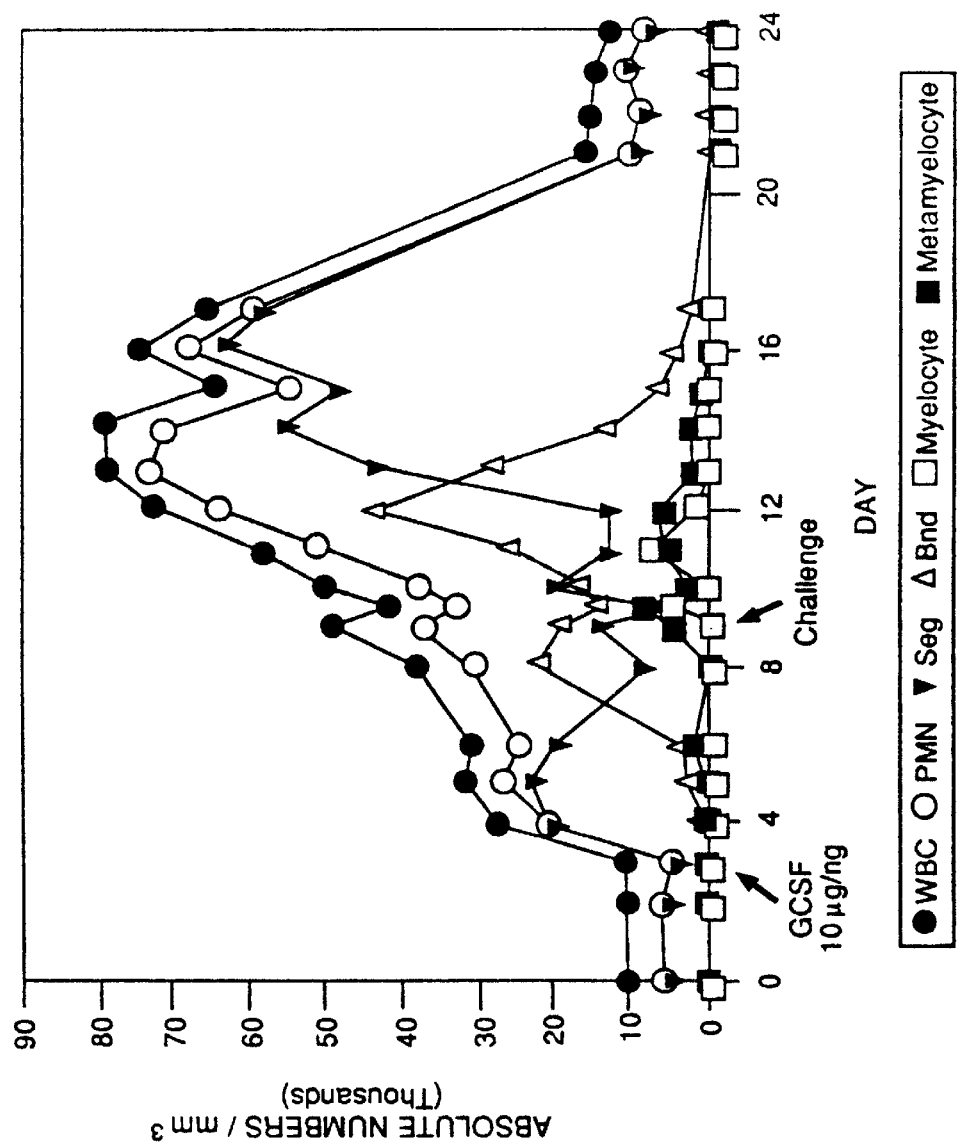
FIGS. 21–23 are graphic representations of results obtained in Example 7 which relate to infection of cows with *Klebsiella Pneumonia.
Figure 22:
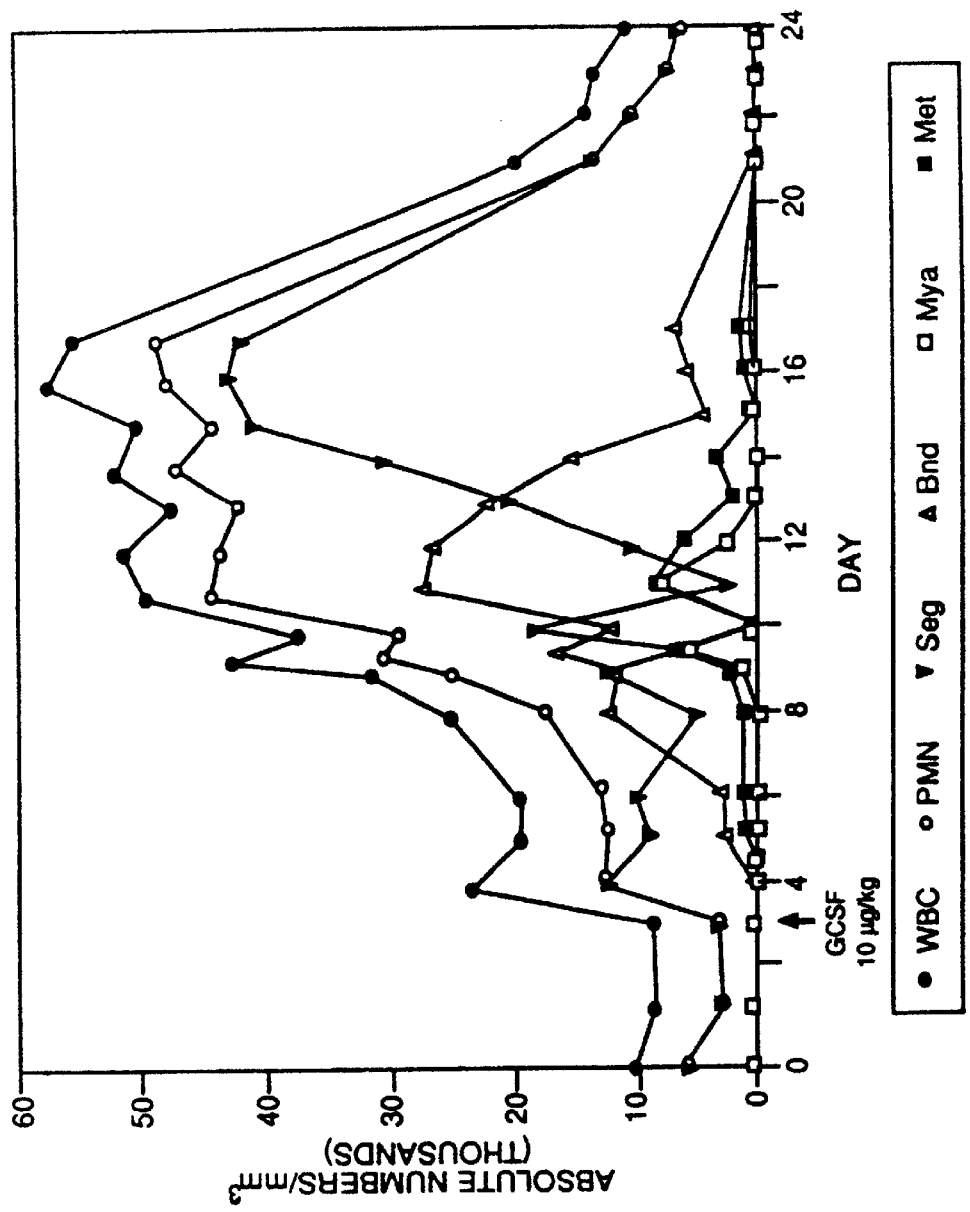
Figure 23:
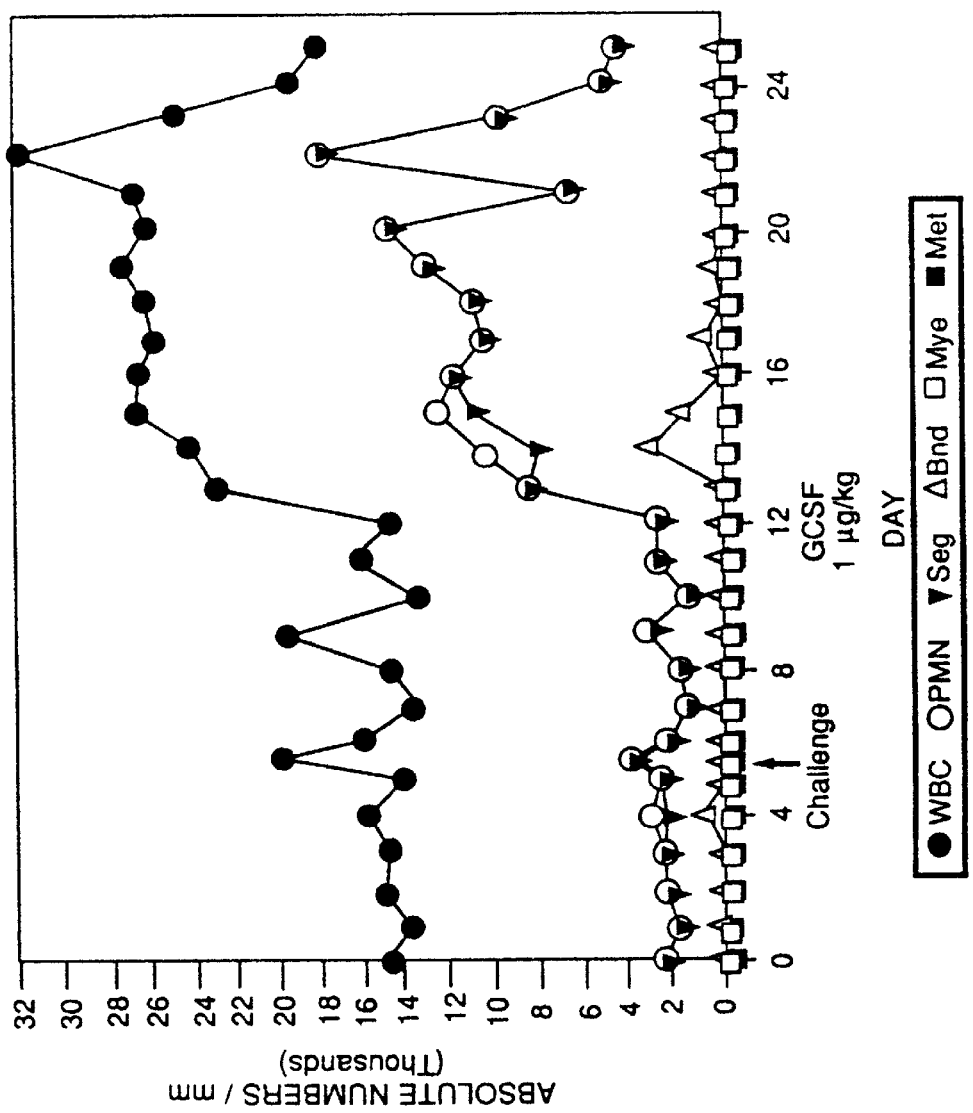

Representative results are shown in FIGS. 21–23.

Twenty-four hours after the challenge, an independent clinician palpitated all 36 udders. The clinician picked out the infected quarters of the 36 total quarters; these were the challenged quarters from the three untreated cows.

EXAMPLE 8

Method for Prevention of Coliform Mastitis

This example is directed to a method using G-CSF in the prevention of coliform mastitis in lactating cows. To test the efficacy of human G-CSF in preventing the clinical effects of coliform mastitis in lactating dairy cows, the cows were given an experimental challenge of a pathogenic *E. coli*.

Twelve mid-lactation Holstein dairy cows were randomly assigned to 1 of 2 groups. Only cows with milk cultures that were negative to coliforms, and with a negative CMT (California Mastitis Test) were used in the experimental study. The two groups were: Group 1 (infected, unmedicated controls) and Group 2 (infected, medicated with 3 µg/kg of G-CSF).

The basic method involved treating the cows with G-CSF (group 2) from days 1–17, then challenging on day 10 and finally, monitoring mortality and morbidity for days 11–21. Group 1 received placebo injections of saline for days 1–17.

The specific schedule was as follows:

| DAY | G-CSF | CBC[1] | CMT[2] | SCC[3] | MILK CULTURE | PLACEBO | BODY TEMPERATURE |
|---|---|---|---|---|---|---|---|
| 0 |  | ✓ | ✓ | ✓ | ✓ |  | ✓ |
| 1 | ✓ |  |  |  |  | ✓ |  |
| 2 | ✓ |  |  |  |  | ✓ |  |
| 3 | ✓ |  |  |  |  | ✓ |  |
| 4 | ✓ |  |  |  |  | ✓ |  |
| 5 | ✓ |  | ✓ |  |  | ✓ | ✓ |
| 6 | ✓ |  |  |  |  | ✓ |  |
| 7 | ✓ |  |  |  |  | ✓ |  |
| 8 | ✓ |  |  |  |  | ✓ |  |
| 9 | ✓ |  | ✓ |  | ✓ | ✓ | ✓ |
| 10 Challenge | ✓ | ✓ | ✓ | ✓ | ✓ | ✓ | ✓ |
| 11 | ✓ |  | ✓ |  | ✓ | ✓ | ✓ |
| 12 | ✓ |  | ✓ |  | ✓ | ✓ | ✓ |

-continued

| DAY | G-CSF | CBC[1] | CMT[2] | SCC[3] | MILK CULTURE | PLACEBO | BODY TEMPERATURE |
|---|---|---|---|---|---|---|---|
| 13 | ✓ |  | ✓ |  |  | ✓ | ✓ |
| 14 | ✓ | ✓ | ✓ | ✓ |  | ✓ | ✓ |
| 15 | ✓ |  | ✓ |  | ✓ | ✓ | ✓ |
| 16 | ✓ |  | ✓ |  |  | ✓ | ✓ |
| 17 | ✓ |  | ✓ |  |  | ✓ | ✓ |
| 18 |  |  | ✓ |  |  |  | ✓ |
| 19 |  |  | ✓ | ✓ |  |  | ✓ |
| 20 |  |  | ✓ |  |  |  | ✓ |
| 21 |  | ✓ | ✓ | ✓ | ✓ |  | ✓ |

[1]Complete Blood Counts,
[2]California Mastitis Test,
[3]Somatic Cell Counts
*Supplied by HMS All cows were observed twice daily (a.m. and p.m.) and abnormal clinical observations (i.e. appetite, signs of inflammation, ambulation, attitude, etc.) were recorded. The cows had their udders examined once daily (a.m.) during the entire study period with abnormal findings recorded. All injections of test and control compositions were administered between 8 a.m. and 10 a.m. The cows were milked twice daily and all milk was discarded. No other medications were administered during the study period.

The challenge consisted of an intramammary infusion of a virulent culture of E. coli in 1 quarter. The challenge was titrated prior to the start of the study to produce moderate morbidity.

The cows were maintained until day 31 (14 days after the last G-CSF dose) and then sold for slaughter. All cows that died during the study were necropsied and disposed of.

Figure 24:
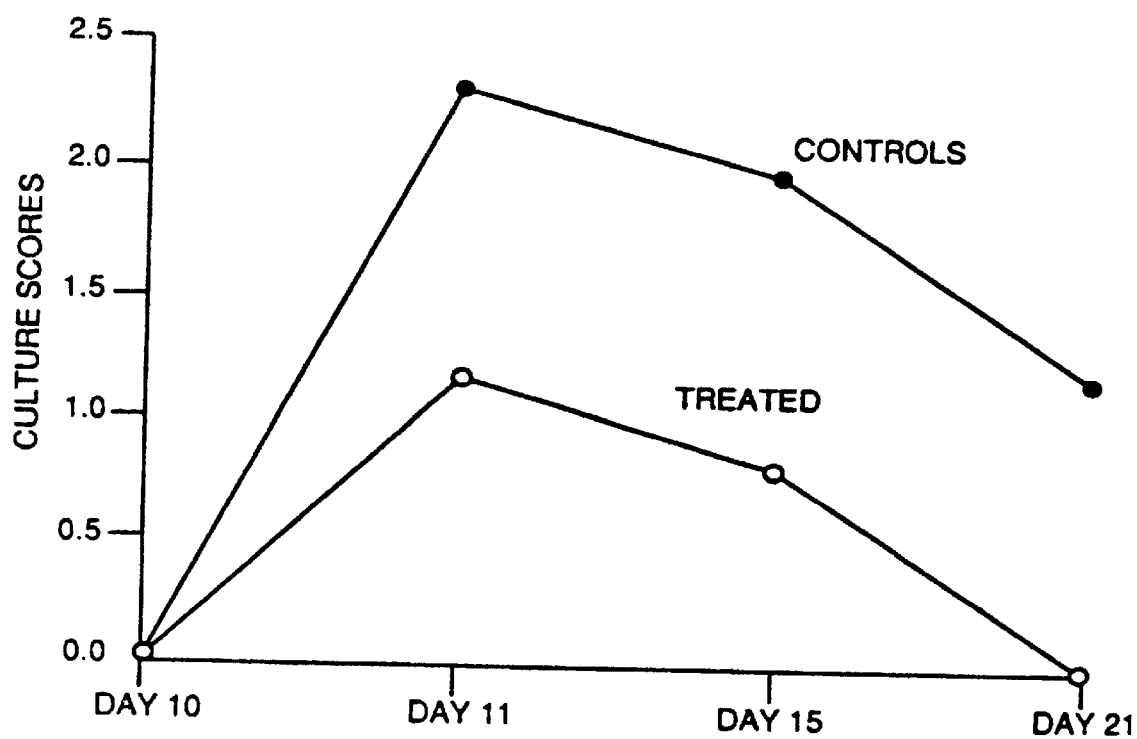
* and FIGS. 24–26 are graphic representations of the results obtained in Example 8 where cows having coliform mastitis were treated with G-CSF.
Figure 25:
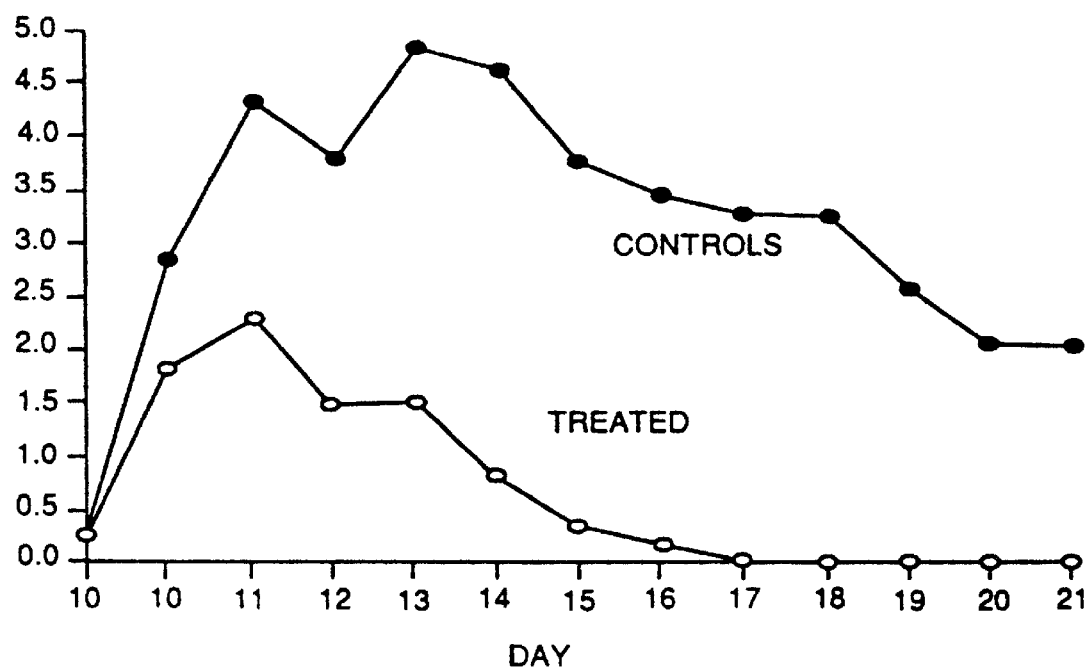
Figure 26:
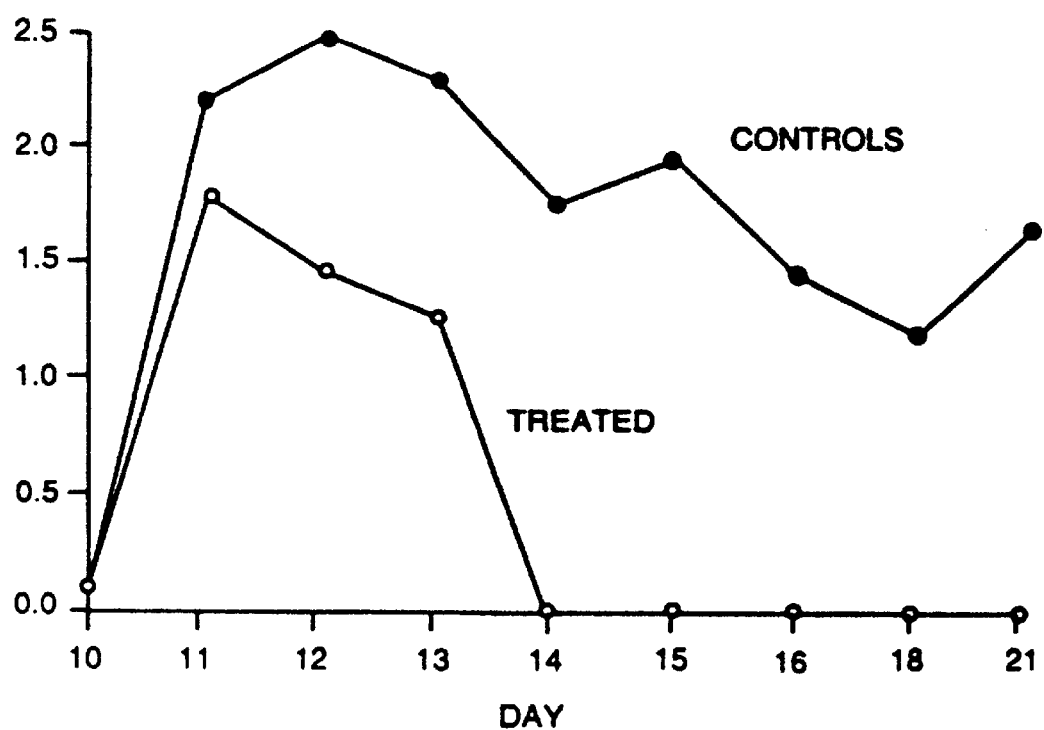

Comparisons between the control and treatment groups were made as to the effectiveness of G-CSF in preventing cows from developing coliform mastitis due to intramammary challenge with E. coli. The results are presented graphically in FIGS. 24 through 26. The results of milk culture scores (1=1–100 E. coli colonies; 2=100–500 E. coli colonies; 3=greater than 500 E. coli colonies) (FIG. 24), clinical scores which are a combination of milk scores (0=normal milk, 1=watery clot, 2=more watery/clot, 3=extremely watery/clot), and udder scores (0=normal, 1=slight swelling/hardness, 2=moderate swelling/hardness, 3=severe swelling/hardness) (FIG. 25), and California Mastitis Test (CMT) (negative and trace=0) scores (FIG. 26), show that treatment with G-CSF under the above described experimental conditions was very effective in lessening the severity and accelerating the recovery of the lactating dairy cows. Thus, an effective mastitis treating amount was shown to be 3 µg/kg.

EXAMPLE 9

Hemogram Changes in Lactating Dairy Cows Given Granulocyte Colony Stimulating Factor Following Induction of Coliform (E. coli) Mastitis.

The original purpose of this study was to determine if treatment with G-CSF would hasten recovery from an experimentally induced mastitis. The inoculations given in this experiment did not result in significant clinical signs and all cows cleared the infection within 24 hrs post inoculation. Hence the therapeutic potential of the G-CSF could not be evaluated. The final objective of this study was to evaluate the hematologic changes induced by human G-CSF at a dose of 3 µg/kg on bovine peripheral blood.

Eight healthy holstein cows in the second half of their lactation were infected with an intramammary inoculation of an E. coli isolate. A mastitis derived E. coli isolate grown for 14–16 hrs in tryptocase soy broth was used. Four of the cows were given G-CSF, the remaining four comprised an infected control group.

An initial intramammary inoculation of 803.7 CFU was given into the right rear quarter. This failed to induce a clinical mastitis. Second and third inoculations of 44,000 CFU and 842,000 CFU, respectively, were given 2 days later and 6 hrs apart. The left rear quarter was used for the second and third inoculations. Time zero was taken from the time of the second inoculation.

Four of these 8 cows were randomly selected and injected subcutaneously with human G-CSF at approximately 6 hrs after inoculation. A single injection was given to each of these cows following the afternoon milking, for the next 4 days. The dose given was 3 µg/kg each time. The remaining 4 E. coli challenged cows received no treatment.

Baseline hematology was obtained on three consecutive days pretreatment and on days 0 to 12 post E. coli inoculation. Blood samples were collected from the tail vein into EDTA containing test tubes.

The hemogram included total white blood cell count (WBC), a differential cell count, total red cell count (RBC), packed cell volume (PCV) and plasma protein (PlPr) determinations. All samples were processed within 3 hrs of collection and differentials were done on Wright Giemsa stained smears. Red and white cell counts were done using a Coulter counter model F.

None of the cows showed systemic signs of illness during the experiment. Around 6 hrs post inoculation the infected quarter of some of the cows became swollen, red and firm. Swelling in the quarters of these cows was only slight by 12 hrs.

Hemograms of the 4 cows given the G-CSF were characterized by a moderate leukocytosis within 24 hrs of the first injection. The noted leukocytosis was predominantly comprised of mature, nontoxic neutrophils. By the second day of treatment, band neutrophils were seen in the peripheral blood. The greatest left shift was $2.5 \times 10^3/\mu l$ bands seen in cow #768. The time at which the maximum left shift occurred corresponded to the time when the segmented neutrophils reached their highest values. The dose intervals were short enough to result in an additive effect of the drug on neutrophil numbers, which did not return to baseline levels between injections. When the injections ceased, the cell count declined at a rate similar to the rate of increase.

Around day 7, the counts fell to a level that was about 2–3 times the baseline value and they remained at this level for the rest of the treatment period.

Maximum total white blood cell counts and segmented neutrophil counts were seen around day 5. The following table shows these cell counts for the treated and untreated groups on day 0 and day 5. The magnitude of the change (%) in cell counts between day 0 and 5 is shown for the treatment group only.

UNTREATED

| | COUNTS (x $10^3/\mu l$) | | | |
|---|---|---|---|---|
| | Day 0 | | Day 5 | |
| COW # | Seg | WBC | Seg | WBC |
| 326 | 3.8 | 11.6 | 2.5 | 8.8 |
| 801 | 2.9 | 8.3 | 2.4 | 7.4 |
| 574 | 4.4 | 11.1 | 1.9 | 6.8 |
| 825 | 3.5 | 10.2 | 2.8 | 8.3 |

G-CSF TREATED

| | COUNTS (x $10^3/\mu l$) | | | | | |
|---|---|---|---|---|---|---|
| | Day 0 | | Day 5 | | % Increase | |
| COW # | Seg | WBC | Seg | WBC | Seg (%) | WBC (%) |
| 768 | 2.9 | 11.7 | 8.9 | 21.2 | 300 | 180 |
| 767 | 4.7 | 10.4 | 21.5 | 28.44 | 500 | 270 |
| 773 | 4.2 | 11 | 22.6 | 32.3 | 500 | 290 |
| 324 | 4.6 | 10.3 | 21.8 | 32.6 | 500 | 320 |

The untreated group had insignificant changes in cell counts between days 0 and 5. The treated group had 3 to 5 fold increases in their neutrophil counts and 2 to 3 fold increases in their WBC counts.

Some of the cows (326,801,574,825,767,768) had a small decline in their WBC count 6 hrs post inoculation.

Cow number 324, of the treated group, had a high normal WBC and PlPr and a low normal PCV, prior to and throughout the experiment. These lab abnormalities along with a mild mucopurulent nasal discharge suggested a chronic disease process. Interestingly, this cow had the greatest increase in neutrophil count (500%) with the smallest maximum left shift (<400/ul).

There were no alterations in the numbers of the other white blood cells in the treated and untreated cows throughout the trial. Also, no alterations were observed in red cell parameters or plasma protein, in either group.

It is concluded that:

1. Human G-CSF stimulates bovine neutrophil granulopoiesis.
2. Human G-CSF given daily at a dose of 3 $\mu g/kg$ causes a 3–5 fold increase in segmented neutrophils after 4 days with only a small left shift.
3. A mild experimentally induced mastitis in one quarter does not impair bone marrow stimulation by the G-CSF.

The following experiments were designed to determine if G-CSF therapy could prevent mortality in animal models of infectious disease.

HAMSTER MODEL OF *PSEUDOMONAS AERUGINOSA* PNEUMONIA

Bacteria

The strain of *P. aeruginosa,* PAO2, used in these experiments was isolated from the blood of a human patient with an abdominal infection. PAO2 was cultured to exponential growth in trypticase soy broth (TSB) (Difco), and aliquots of this culture were then stored frozen at −70° C. in 40% glycerol until used. 1.5 ml aliquots of PAO2 were thawed, added to 50 ml of TSB and incubated 4 hr in shaker flasks at 37° C. Log-phase organisms were harvested by centrifugation at 2000 X g, washed twice with sterile 0.9% saline, and resuspended to the desired concentration as determined spectrophotometrically. All bacterial inocula were confirmed by quantitative cultures using a spiral plating instrument (Spiral Systems, Cincinnati).

Animals

Virus antibody free female Golden Syrian hamsters weighing 80 to 100 grams were obtained from Charles River Canada (Quebec) and quarantined for 5 days. Groups of 5 animals were housed in cages equipped with individual filter bonnets. Animals were allowed unrestricted access to water and a standard hamster food (Tecklad, Winfield, Iowa) until the evening prior to infection. Animals were then fasted overnight. Human recombinant Granulocyte Colony Stimulating Factor (G-CSF) or vehicle (5% dextrose in sterile water) was administered subcutaneously in a total volume of 0.1ml. Animals were administered G-CSF or vehicle on a twice daily (bid) schedule at approximately 8 AM and 3 PM. Injections of G-CSF were continued in surviving animals for 3 days following infection. Animals were infected between 12 and 2 PM.

For intratracheal inoculation, hamsters were anesthetized intraperitoneally with 75mg/kg Nembutal (50 mg/ml; Abbott). Animals were placed on a 30 degree incline board, jaws were opened, and 0.25 ml of the bacterial suspension was administered into the trachea using a curved 22 gauge needle with a blunted tip 2.5 inches long. Following bacterial inoculation the animals were gently shaken for 15 seconds to distribute the inoculum. Animals were allowed to recover from the anesthesia on 37° C. heating pads. Only animals which recovered from the anesthesia were used in the experiment. Animals were observed regularly. Animals displaying symptoms of extreme morbidity (inability to walk or remain upright) were euthanized by a blinded observer and counted as a death.

EXAMPLE 10

Figure 27:
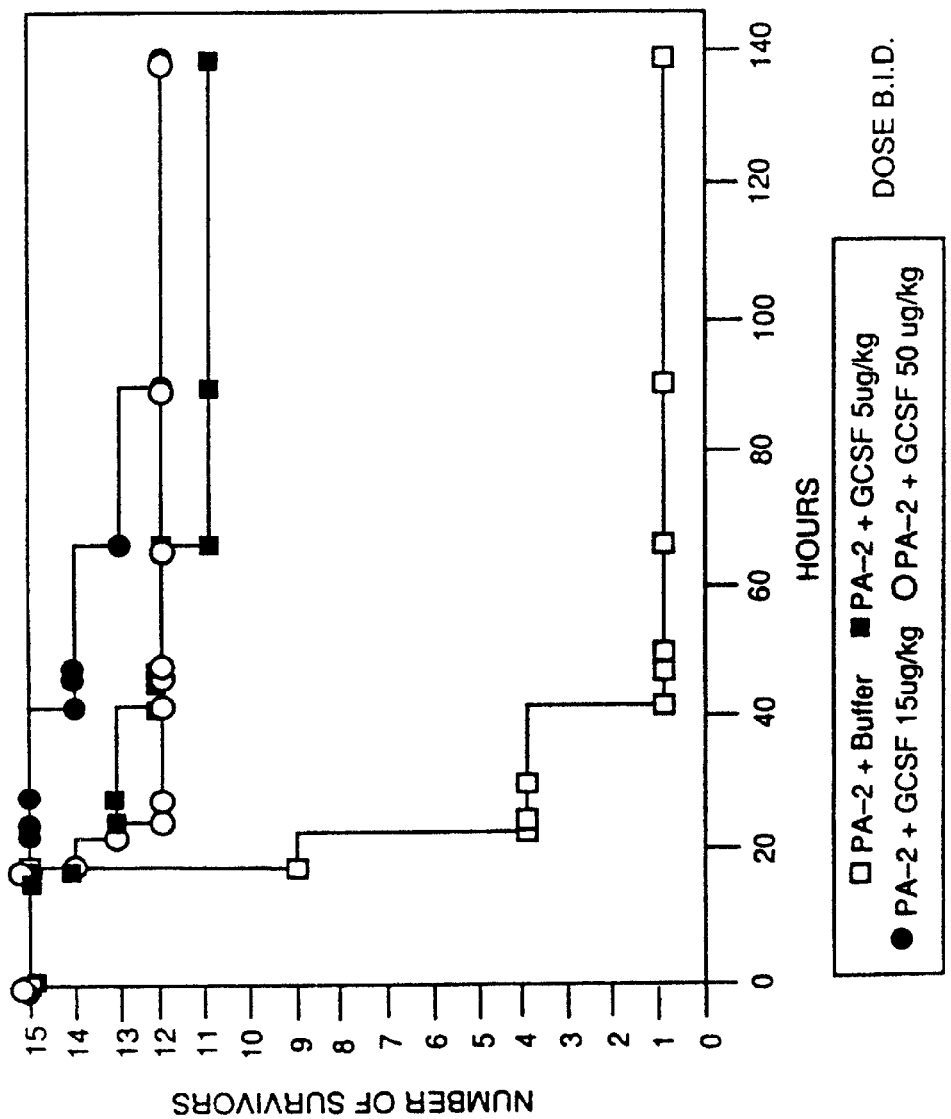
FIGS. 27–29 are graphic representations of the results obtained in Examples 10–12.

The Use of G-CSF as a Prophylactic/Therapeutic Agent for the Prevention of Bacterial Pneumonia in Hamsters The purpose of this experiment was to determine the efficacy of various doses of G-CSF in preventing a fatal respiratory infection caused by *Pseudomonas aeruginosa.* The groups were as follows (15 hamsters/group):

Group 1: Infected, unmedicated (vehicle only)
Group 2: Infected, medicated with G-CSF 5 ug/kg bid
Group 3: Infected, medicated with G-CSF 15 ug/kg bid
Group 4: Infected, medicated with G-CSF 50 ug/kg bid Dosing of animals was begun on the day prior to bacterial challenge. Thus, animals received 3 doses prior to infection, and surviving animals continued to receive G-CSF bid. Approximately $5 \times 10^7$ colony forming units (CFU) of PAO2 were administered to each hamster. FIG. 27 shows the relative mortality in each group with time. All three groups of hamsters which received G-CSF had significantly less mortality than those animals which received vehicle only.

There was a significant treatment effect (p<0.001) for all groups by Log Rank Chi Square Analysis. Hamsters pretreated with G-CSF 5 μg/kg bid prior to infection did not have a significantly decreased mortality rate as compared to control animals. However, animals pretreated with 15 μg/kg G-CSF bid did differ significantly from controls (p<0.001). Animals receiving 50 μg/kg bid G-CSF also had significantly decreased mortality (p<0.001). The 15 μg/kg bid and 50 μg/kg bid doses were not signficantly different from each other.

EXAMPLE 11

Effect of G-CSF Dosing Schedule on Mortality Rate of Hamsters With a *Pseudomonas aeruginosa* Lung Infection The purpose of this experiment was to determine the amount of time required between commencement of G-CSF therapy and infectious challenge to effect diminished mortality.

Group 1: Infected, unmedicated (vehicle only)

Group 2: Infected, medicated 15 μg/kg bid beginning approximately 30 hours prior to infection. Animals received 3 doses of G-CSF prior to challenge.

Group 3: Infected, medicated 15 μg/kg bid beginning 5 hours prior to challenge.

Figure 28:
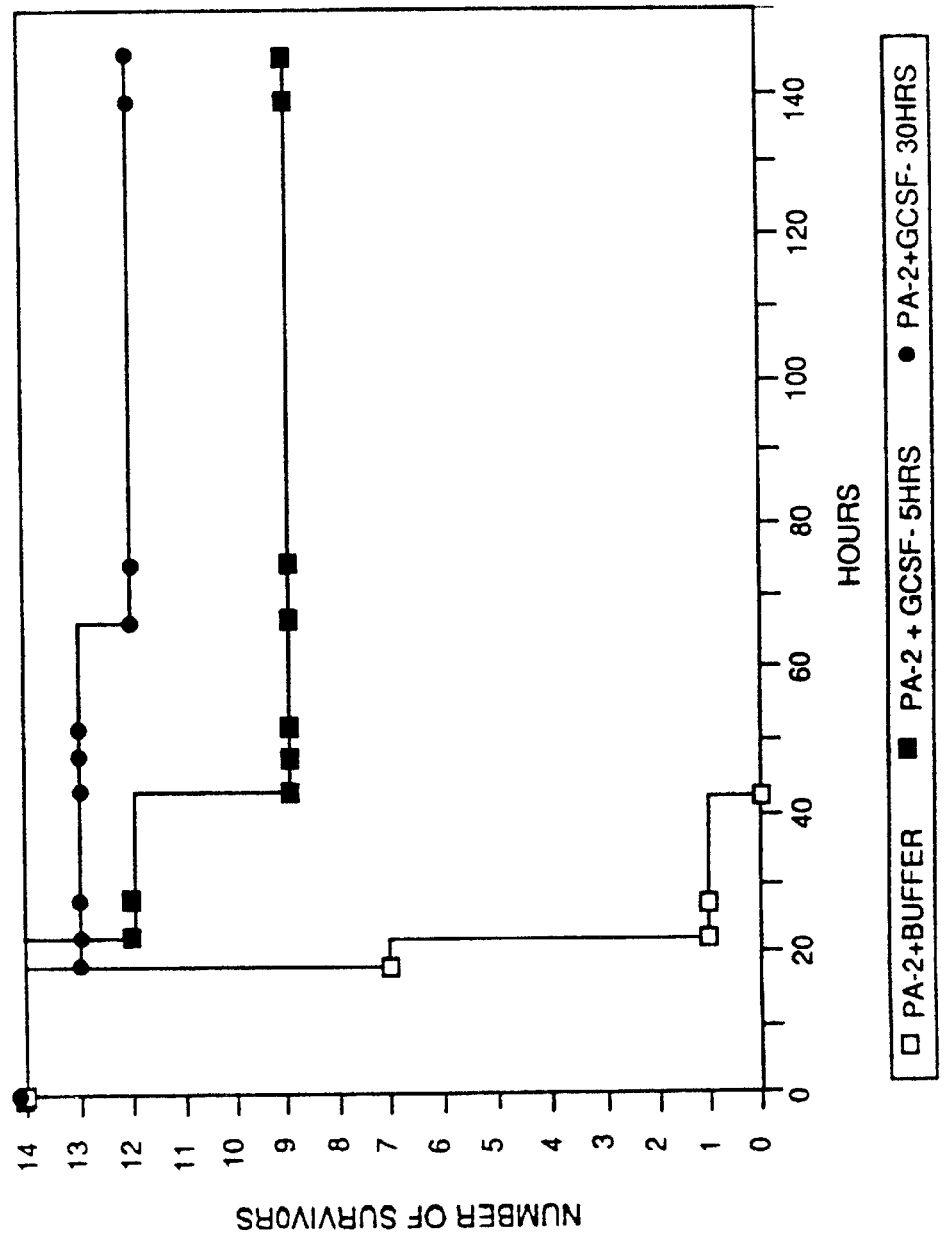

Animals received approximately $5 \times 10^7$ CFU of PAO2 intratracheally. Dosing with G-CSF continued on the bid schedule for 3.5 days in surviving animals. FIG. 28 shows the mortality with time in all groups of animals. Both medicated groups had significantly reduced mortality compared to nonmedicated animals.

There was a significant treatment effect (p<0.001) for all groups by Log Rank Chi Square analysis. Hamsters pretreated 5 hours before infection had a significantly decreased mortality (p<0.001) as compared to control animals. Hamsters pretreated 30 hours before infection were also significantly different (p<0.001) from control animals.

Rat Model of *Candida Albicans* Pyelonephritis

Organism

The clinical isolate of *Candida albicans* used in this experiment was maintained on Sabouraud dextrose agar slants. *C. albicans* was cultured overnight in Sabouraud dextrose broth. *C. albicans* was isolated by centrifugation at 2000 X g for 10 min at 4° C. The pellet was washed twice with phosphate buffered saline (PBS) resuspended in PBS, and adjusted to the desired concentration after enumeration using a hemocytometer. All inocula were confirmed by quantitative cultures.

Animals

Female Sprague-Dawley rats weighing 150–200 grams, obtained from Harlan-Sprague-Dawley, Inc. (Indianapolis, Ind.), were quarantined for 5 days. Groups of 4 animals were housed in hanging wire cages allowed unrestricted access to standard rat food and water. Animals received G-CSF or vehicle (PBS) twice daily beginning the day prior to the infection challenge. Surviving animals continued to receive G-CSF or vehicle bid for 10 days.

For intravenous inoculation, rats were anesthetized with ether. A 0.1 ml volume *C. albicans* was injected into the tail vein.

Group 1: Infected, unmedicated (vehicle only)

Group 2: Infected, medicated with G-CSF 50 ug/kg bid Beginning approximately 30 hours prior to infection.

Figure 29:
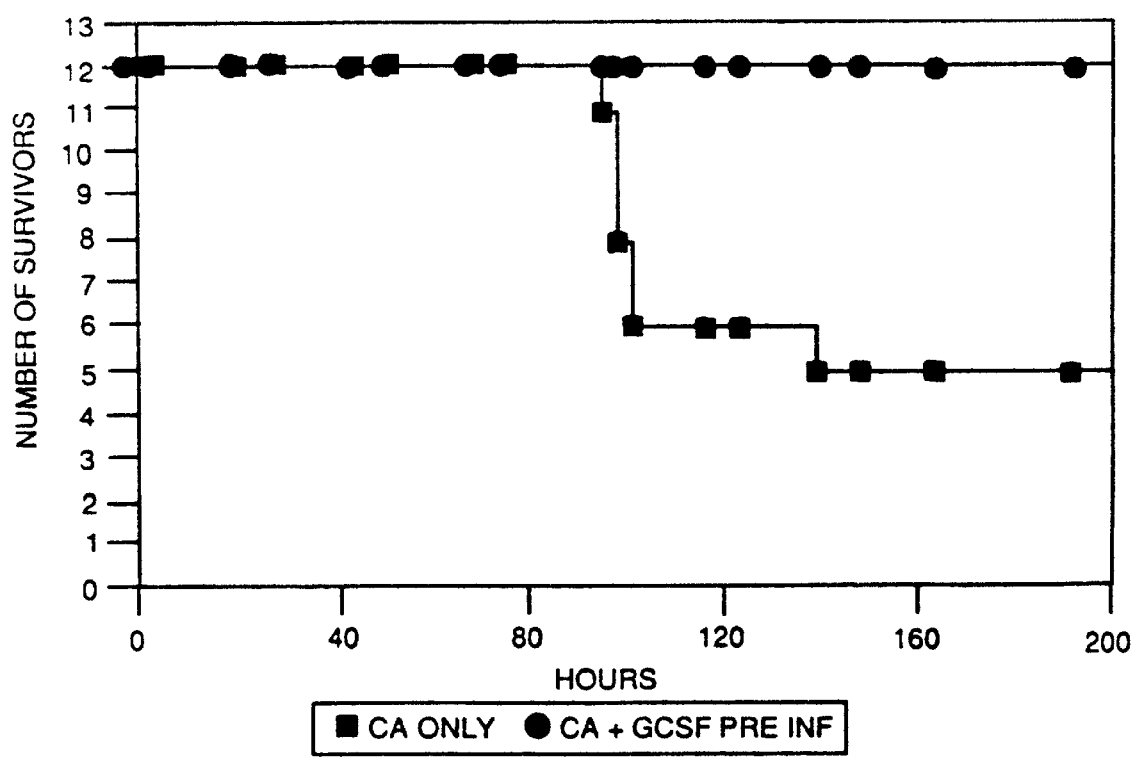

FIG. 29 shows the mortality with time in each group of animals. Animals received $1.3 \times 10^6$ CFU of *C. albicans*. There were no deaths in the group which received G-CSF.

There was a significant treatment effect (p<0.01l) for all groups by Log Rank Chi Square Analysis. G-CSF pretreated animals had a significantly decreased mortality rate from control animals (p<0.001). Rats treated with G-CSF post infection did not differ significantly from the controls.

EXAMPLE 12

G-CSF Administered to Growing Pigs

Bovine G-CSF was administered to growing pigs (~30kg) as follows:

Dosage=5 μg/kg body weight/day

Route: subcutaneous n=6 pigs

The neutrophil levels were as shown below:

| Day | Neutrophils (Avg) |
|---|---|
| 0 | 3108 |
| 2 | 29922 |
| 4 | 24595 |
| 6 | 42713 |

In a study in 6 normal growing pigs, neutrophil levels increased dramatically within 2 days and reached a 13 fold higher level after 6 days of daily administration.

EXAMPLE 13

G-CSF Administered to Normal Neonatal Foals

Bovine G-CSF was administered to normal neonatal foals commencing at 1 day of age as follows:

Dosage=10 and 20 μg/kg body weight/day

Route: intramuscular n=5 foals

Day 0=day prior to first G-CSF administration

The neutrophil level was as shown below:

| Foal No. | Dose (μg/kg) | Neutrophil Count | | | | | |
|---|---|---|---|---|---|---|---|
| | | Day 0 | Day 1 | Day 2 | Day 3 | Day 4 | Day 5 |
| 1 | 20 | 4950 | 17473 | 28072 | 35524 | 30874 | 38263 |
| 2 | 10 | 6708 | 16195 | 27807 | 28560 | 26960 | 26535 |
| 3 | 10 | 5016 | 10472 | 6715 | 16112 | 19975 | 16464 |
| 4 | 10 | 6480 | 6225 | 4400 | 5610 | 10332 | 15372 |
| 5 | 10 | 9156 | 10406 | 11692 | 11304 | 13588 | 17300 |

In a study of 5 neonatal foals given bovine G-CSF daily, neutrophil levels increased up to three and one-half fold within 24 hours and up to seven and one-half fold after 5 days, depending on dosage.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A process for isolating and purifying granulocyte colony stimulating factor (G-CSF) from a G-CSF producing microorganism consisting of:

1) lysing the microorganism and separating insoluble material containing G-CSF from soluble proteinaceous material;

2) solubilizing and oxidizing the G-CSF in the presence of a denaturant solubilizing agent and an oxidizing agent;

3) removing the denaturant solubilizing agent from the G-CSF;

4) subjecting the G-CSF to ion exchange chromatography; and 5) recovering purified G-CSF.

2. A process according to claim 1 wherein the G-CSF is met-hG-CSF.

3. A process according to claim 1 wherein step 4) ion exchange chromatography step is an anion exchange chromatography step followed by cation exchange chromatography.

4. A process according to claim 1 wherein the denaturant solubilizing agent of step 2) is Sarkosyl.

5. A process according to claim 1 wherein the oxidizing agent is $CUSO_4$.

6. A process according to claim 1 wherein step 3) the denaturant solubilizing agent is removed using Dowex.

7. A process for isolating and purifying granulocyte colony stimulating factor (G-CSF) from a G-CSF producing microorganism consisting of:

1) lysing the microorganism and separating insoluble material containing G-CSF from soluble proteinaceous material;

2) extracting the material with deoxycholate;

3) solubilizing and oxidizing the G-CSF in the presence of a denaturant solubilizing agent and an oxidizing agent;

4) removing the denaturant solubilizing agent from the G-SCF;

5) subjecting the G-CSF to ion exchange chromatography; and 6) recovering the purified G-CSF.

* * * * *